US011525796B2

(12) United States Patent
Yeo et al.

(10) Patent No.: US 11,525,796 B2
(45) Date of Patent: Dec. 13, 2022

(54) MICROTUBE SENSOR FOR PHYSIOLOGICAL MONITORING

(71) Applicant: National University of Singapore, Singapore (SG)

(72) Inventors: Joo Chuan Yeo, Singapore (SG); Wang Xi, Singapore (SG); Longteng Yu, Singapore (SG); Chwee Teck Lim, Singapore (SG)

(73) Assignee: National University of Singapore, Singapore (SG)

( * ) Notice: Subject to any disclaimer, the term of this patent is extended or adjusted under 35 U.S.C. 154(b) by 331 days.

(21) Appl. No.: 16/487,983

(22) PCT Filed: Feb. 19, 2018

(86) PCT No.: PCT/SG2018/050076
§ 371 (c)(1),
(2) Date: Aug. 22, 2019

(87) PCT Pub. No.: WO2018/160135
PCT Pub. Date: Sep. 7, 2018

(65) Prior Publication Data
US 2020/0025699 A1    Jan. 23, 2020

Related U.S. Application Data

(60) Provisional application No. 62/465,002, filed on Feb. 28, 2017.

(51) Int. Cl.
*G01N 27/06* (2006.01)
*A61B 5/021* (2006.01)
(Continued)

(52) U.S. Cl.
CPC ......... *G01N 27/06* (2013.01); *A61B 5/02108* (2013.01); *A61B 5/02444* (2013.01);
(Continued)

(58) Field of Classification Search
None
See application file for complete search history.

(56) References Cited

U.S. PATENT DOCUMENTS 5,241,300 A * 8/1993 Buschmann ......... A61B 5/1135
340/531
11,161,736 B2    11/2021 Xi et al.
(Continued)

FOREIGN PATENT DOCUMENTS

CN    1930513    3/2007
CN    103331754    10/2013
(Continued)

OTHER PUBLICATIONS

Avolio, A. P., et al., "Role of Pulse Pressure Amplification in Arterial Hypertension", Hypertension 2009, 54, 375.
(Continued)

*Primary Examiner* — Daniel L Cerioni
*Assistant Examiner* — Samuel C Kim
(74) *Attorney, Agent, or Firm* — Hamilton, Brook, Smith & Reynolds, P.C.

(57) ABSTRACT

A soft, flexible microtube sensor and associated method of sensing force are described. A liquid metallic alloy is sealed within a microtube as thin as a strand of human hair to form the physical force sensing mechanism. The sensor is hardly distinguishable with the naked eye, and can be used for the continuous biomonitoring of physiological signals, such as unobtrusive pulse monitoring. Also described is a method of fabricating the microtube sensor and wearable devices incorporating one or more microtube sensors.

20 Claims, 15 Drawing Sheets

(51) Int. Cl.
*A61B 5/024* (2006.01)
*G01L 1/24* (2006.01)
(52) U.S. Cl.
CPC ........ *G01L 1/245* (2013.01); *A61B 2562/028* (2013.01); *A61B 2562/0261* (2013.01)

(56) References Cited

U.S. PATENT DOCUMENTS

| | | | |
|---|---|---|---|
| 2007/0013869 A1 | 1/2007 | Dahi et al. | |
| 2010/0154556 A1* | 6/2010 | Yin | G01B 7/18 |
| 2012/0075069 A1* | 3/2012 | Dickey | G01L 1/205 340/10.1 |
| 2015/0351967 A1 | 10/2015 | Lim et al. | |
| 2019/0062152 A1 | 2/2019 | Xi et al. | |
| 2020/0003638 A1* | 1/2020 | Visell | G01L 1/205 |

FOREIGN PATENT DOCUMENTS

| | | |
|---|---|---|
| CN | 104340956 | 2/2015 |
| CN | 104445055 | 3/2015 |
| CN | 104936566 | 9/2015 |
| CN | 105444928 | 3/2016 |
| CN | 106197773 | 12/2016 |
| EP | 1557396 | 7/2005 |
| JP | S62192171 A | 8/1987 |
| JP | H5304021 | 11/1993 |
| JP | H07328127 A | 12/1995 |
| JP | 2008248181 A | 10/2008 |
| JP | 2009537439 A | 10/2009 |
| WO | WO 2011/028579 | 3/2011 |
| WO | WO 2013/044226 | 3/2013 |
| WO | WO 2016/019087 | 2/2016 |
| WO | WO 2017/151915 | 9/2017 |
| WO | 2018144589 A1 | 8/2018 |

OTHER PUBLICATIONS

Cai, F., et al., "Ultrasensitive, passive and wearable sensors for monitoring human muscle motion and physiological signals", Biosensors and Bioelectronics 77 (2016) 907-913.
Chen, L. Y., et al., "Continuous Wireless Pressure Monitoring and Mapping with Ultra-Small Passive Sensors for Health Monitoring and Critical Care", Nat. Commun. 2014, 5.
Deguchi, S., et al., "Viscoelastic and optical properties of four different PDMS polymers", Journal of Micromechanics and Microengineering 2015, 25, 097002, 7 pages.
Do, T. N. et al., Stretchable, Twisted Conductive Microtubules for Wearable Computing, Robotics, Electronics, and Healthcare. *Scientific Reports*, May 11, 2017, vol. 7, No. 1753, pp. 1-12.
Gong, S., et al., "A wearable and highly sensitive pressure sensor with ultrathin gold nanowires", Nature Communications 2014, 5, 3132.
Grilli, S., et al., "3D lithography by rapid curing of the liquid instabilities at nanoscale", Proceedings of the National Academy of Sciences 2011, 108, 15106.
Harada, S., et al., "Fully Printed Flexible Fingerprint-like Three-Axis Tactile and Slip Force and Temperature Sensors for Artificial Skin", ACS Nano 2014, 8 (12), 12851-12857.
International Search Report for International Application No. PCT/SG2018/050076, "Microtube Sensor For Physiological Monitoring", dated May 14, 2018.
International Search Report for International Application No. PCT/SG2018/050076, "Microtube Sensor For Physiological Monitoring", dated Sep. 12, 2019.
Johnston, I. D., et al., "Mechanical characterization of bulk Sylgard 184 for microfluidics and microengineering", Journal of Micromechanics and Microengineering 2014, 24, 035017.
Lee, H. K.; et al., "Normal and Shear Force Measurement Using a Flexible Polymer Tactile Sensor With Embedded Multiple Capacitors", Journal of Microelectromechanical Systems 2008, 17 (4), 934-942.
Li, R., et al., "Microflotronics: A Flexible, Transparent, Pressure-Sensitive Microfluidic Film", Advanced Functional Materials 2014, 24, 6195-6203.
Li, Y., et al., "Cellulose-Nanofiber-Enabled 3D Printing of a Carbon-Nanotube Microfiber Network", Small Methods (2017), 1 (10), 1700222 (8 pages).
Li, Y., et al., "Highly Conductive Microfiber of Graphene Oxide Templated Carbonization of Nanofibrillated Cellulose", Adv. Funct. Mater. 2014, 24 (46), 7366-7372.
Liu, T., et al., "A Small and Low-Cost 3-D Tactile Sensor for a Wearable Force Plate", IEEE Sensors Journal 2009, 9 (9), 1103-1110.
Nichols, W.W., "Clinical Measurement of Arterial Stiffness Obtained from Noninvasive Pressure Waveforms", American Journal of Hypertension 2005, 18, 3S.
Park, D. Y., et al., "Self-Powered Real-Time Arterial Pulse Monitoring Using Ultrathin Epidermal Piezoelectric Sensors", Adv. Mater. 2017, 29 (37).
Park, Y.-L., et al., "Hyperelastic pressure sensing with a liquid-embedded elastomer", Journal of Micromechanics and Microengineering 2010, 20 (12), 125029.
Quéré, D., "Fluid Coating on a Fiber", Annual Review of Fluid Mechanics 1999, 31, 347-384.
Silverman, I. K., et al., "Displacements in closed circular rings subject to concentrated diametral loads", Journal of the Franklin Institute, 279(5), May 1965, 374-386.
Written Opinion for International Application No. PCT/SG2018/050076, "Microtube Sensor For Physiological Monitoring", dated May 14, 2018.
Xi, W., et al., "Soft Tubular Microfluidics for 2D and 3D Applications", Proc. Natl. Acad. Sci. 2017, 114 (40), 10590-10595.
Yan H., et al., "Coaxial printing method for directly writing stretchable cable as strain sensor", *Appl. Phys. Lett.*, Aug. 23, 2016, vol. 109, pp. 083502-1-083502-4.
Yang, T. et al., "A Wearable and Highly Sensitive Graphene Strain Sensor for Precise Home-Based Pulse Wave Monitoring", ACS Sensors 2017, 2 (7), 967-974.
Yun, Y. J. et al., "Highly Conductive and Environmentally Stable Gold/graphene Yarns for Flexible and Wearable Electronics", Nanoscale 2017, 9 (32), 11439-11445.
Zhu, S. et al., "Ultrastretchable Fibers with Metallic Conductivity Using a Liquid Metal Alloy Core", Advanced Functional Materials 2013, 23 (18), 2308-2314.
Abdelgawad, M., et al., "A fast and simple method to fabricate circular microchannels in polydimethylsiloxane (PDMS)", Lab Chip 2011, 11 (3), 545-551.
Aboutalebi, S.H., et al., "High-Performance Multifunctional Graphene Yarns: Toward Wearable All-Carbon Energy Storage Textiles", ACS Nano, 2014, 11 pgs.
Atencia, J., et al., "Controlled microfluidic interfaces", Nature 2005, 437 (7059), 648-655.
Atwa, Y., et al., "Silver nanowire coated threads for electrically conductive textiles", J. Mater. Chem. C., 2015, 3, 3908-3912.
Au, A. K., et al., "3D-printed microfluidic automation", Lab Chip 2015, 15 (8), 1934-1941.
Au, A. K., et al., "Mail-order microfluidics: evaluation of stereolithography for the production of microfluidic devices", Lab Chip 2014, 14 (7), 1294-1301.
Bao, Z., et al., "Flexible and Stretchable Devices", Adv. Mater, 2016, 28, 4177-4179. (Jun. 6, 2016).
Bhargava, et al., N., "Discrete elements for 3D microfluidics", Proc. Natl. Acad. Sci. USA 2014, 111 (42), 15013-15018.
Bhatia, S. N., et al., "Microfluidic organs-on-chips", Nat. Biotech. 2014, 32 (8), 760-772.
Cai, G., et al., "Extremely Stretchable Strain Sensors Based on Conductive Self-Healing Dynamic Cross-Links Hydrogels for Human-Motion Detection", Adv. Sci. 2017, 4, 1600190.
Cantat, I., et al., "Lift Force and Dynamical Unbinding of Adhering Vesicles under Shear Flow", Phys. Rev. Lett. 1999, 83 (4), 880-883.
Choong, C-L., et al., "Highly Stretchable Resistive Pressure Sensors Using a Conductive Elastomeric Composite on a Micropyramid Array", Adv. Mater. 2014, 26, 3451-3458.

(56) References Cited

OTHER PUBLICATIONS

Chortos, AI., et al., "Pursuing prosthetic electronic skin", Nature Materials vol. 15, Sep. 2016, 937-950.
Colas, A., "Silicone Biomaterials: History and Chemistry", Chimic Nouvelle 1990, 8 (30), 847.
Davis, J. A., et al., "Deterministic hydrodynamics: Taking blood apart", Proc. Natl. Acad. Sci. USA 2006, 103 (40), 14779-14784.
De Ville, M., et al., "Simple and low-cost fabrication of PDMS microfluidic round channels by surface-wetting parameters optimization", Microfluid Nanofluid, 2012, 12 (6), 953-961.
Derby, B., "Printing and Prototyping of Tissues and Scaffolds", Science 2012, 338 (6109), 921-926.
Di Carlo, D., et al., "Continuous inertial focusing, ordering, and separation of particles in microchannels", Proc. Natl. Acad. Sci. USA 2007, 104 (48), 18892-18897.
Englert, D. L., et al., "Investigation of bacterial chemotaxis in flow-based microfluidic devices", Nat. Protocols 2010, 5 (5), 864-872.
Extended Search Report for European Application No. 17760815.5, "Versatile, Flexible And Biocompatible Elastomeric Microtubes", dated Sep. 10, 2019.
Gao, W., et al., "Fully integrated Wearable sensor arrays for multiplexed in situ perspiration analysis", Nature, Jan. 28, 2016; 529(7587): 509-514.
Goldsmith, H. L., et al., "Margination of leukocytes in blood flow through small tubes", Microvasc. Res. 1984, 27 (2), 204-222.
Gong, S., et al., "Tattoolike Polyaniline Microparticle-Doped Gold Nanowire Patches as Highly Durable Wearable Sensors", ACS Appl. Mater. Interfaces, Aug. 2015, 9 pages.
Gorissen, B., et al., "Modeling and bonding-free fabrication of flexible fluidic microactuators with a bending motion", J. Micromech. Microeng. 23 (2013) 045012 (10 pp).
H. Lee, D.-H. Kim, "Soft bioelectronics using nanomaterials", 2016.
Hammock, M.L., et al., "25th Anniversary Article: The Evolution of Electronic Skin (E-Skin): A Brief History, Design Considerations and Recent Progress" Adv. Mater. 2013, 25, 5997-6038.
Han, S., et al., "Mechanically Reinforced Skin-Electronics with Networked Nanocomposite Elastomer", Adv. Mater. 2016, 28, 10257-10265, (Oct. 7, 2016).
Harazim, S. M., et al., "Lab-in-a-tube: on-chip integration of glass optofluidic ring resonators for label-free sensing applications", Lab Chip 2012, 12 (15), 2649-2655.
Heng, X., et al., "Flexible PDMS microtubes for examining local hydrophobicity ", Microsyst Technol (2015) 21: 477-485.
Hou, H. W., et al., "Isolation and retrieval of circulating tumor cells using centrifugal forces", Sci. Rep. 2013, 3, 1-8.
Huang, S., et al., "Electroeposition of polypyrrole on carbon nanotube-coated cotton fabrics for all-solid flexible supercapacitor electrodes", Royal Society of Chemistry, 2013, 8 pages.
Hyun, W.J., et al., "High-Resolution Patterning of Graphene by Screen Printing with a Silicon Stencil for Highly Flexible Printed Electronics", Adv. Mater. 2015, 27, 109-115.
International Search Report and Written Opinion of the International Searching Authority for International Application No. PCT/US2017/20443, entitled "Versatile, Flexible And Biocompatible Elastomeric Microtubes," dated May 16, 2017.
Jang, K-I., et al., "Rugged and breathable forms of stretchable electronics with adherent composite substrates for transcutaneous monitoring", Nat. Commun., 5:4779 doi: 10.1038/ncommos5779 (2014).
Jinno, H., et al., "Stretchable and waterproof elastomer-coated organic photovoltaics for washable electronic textile applications", Nature Energy, (Sep. 2017), 6 pages.
Kalpakli, A. "Experimental study of turbulent flows through pipe bends", PhD Thesis, KTH Mechanics, Stockholm, Sweden, 2012.
Kalpakli, A., et al., "Dean vortices in turbulent flows: rocking or rolling?", J Vis 2012, 15 (1), 37-38.
Kang, S-K., et al., "Bioresorbable silicon electronic sensors for the brain", Nature, (2016) 1-9.

Kenry, et al., "Emerging flexible and wearable physical sensing platforms for healthcare and biomedical applications", Microsystems & Nanoengineering (2016) 2, 16043; doi:10.1038/micronano.2016.43.
Khondoker, M.A.H., et al., "Fabrication methods and applications of microstructured gallium based liquid metal alloys", Smart Mater. Struct. 25 (2016) 093001, 23 pages.
Kim, J., et al., "Stretchable silicon nanoribbon electronics for skin prosthesis", Nat. Commun., 5:5747 doi: 10.1038/ncomms6747 (2014).
Kim., D-H., "Epidermal Electronics", Science, 333, 838 (2011).
Kim., S., et al., "Stretching and Twisting Sensing with Liquid-Metal Strain Gauges Printed on Silicone Elastomers", IEEE Sensors Journal, Nov. 2015, 15(11): 6077-6078.
Kitson, P. J., et al., "Configurable 3D-Printed millifluidic and microfluidic 'lab on a chip' reactionware devices", Lab Chip 2012, 12 (18), 3267-3271.
Kolesky, D. B., et al., "3D Bioprinting of Vascularized, Heterogeneous Cell-Laden Tissue Constructs", Adv. Mater. 2014, 26 (19), 3124-3130.
Kumar, A., et al., "Mechanism of Margination in Confined Flows of Blood and Other Multicomponent Suspensions", Phys. Rev. Lett. 2012, 109 (10), 108102.
Le Floch, P., et al., "Wearable and Washable conductors for active textiles", ACS Applied Materials & Interfaces (Jul. 2011), Doi:10.1021/acsami.7b07361.
Lee, J., et al., "Conductive Fiber-Based Ultrasensitive Textile Pressure Sensor for Wearable Electronics", Adv. Mater., 2015, 27, 2433-2439.
Lee, J., et al., "Elastomeric micro wire-based optical gas flowmeter with stretching-enabled tunability in measurement range", Opt. Lett. 2011, 36 (19), 3789-3791.
Lee, J., et al., "Sucrose-based fabrication of 3D-networked, cylindrical microfluidic channels for rapid prototyping of lab-on-a-chip and vaso-mimetic devices", Lab Chip 2012, 12 (15), 2638-2642.
Li, S., et al., "A Stretchable Multicolor Display and Touch Interface Using Photopatterning and Transfer Printing", Adv. Mater. 2016, 28, 9770-9775. (Sep. 22, 2016).
Marin, S., et al., "Nanomaterials Based Electrochemical Sensing Applications for Safety and Security", Electroanalysis 2012, 24(3): 459-469.
Matsuhisa, N., et al., "Printable elastic conductors by in situ formation of silver nanoparticlcs from silver flakes", Nature Materials, (May 2017), 8 pages.
Matsuhisa, N., et al., "Printable elastic conductors with a high conductivity for electronic textile applications", Nature Communications, 6:7461, DOI: 10.1038/ncommas8461 (2015).
Miller, J. S., et al., "Rapid casting of patterned vascular networks for perfusable engineered three-dimensional tissues", Nat. Mater. 2012, 11 (9), 768-774.
Notification Concerning Transmittal of International Preliminary Report on Patentability for International Application No. PCT/US2017/020443, "Versatile, Flexible and Biocompatible Elastomeric Microtubes", dated Sep. 13, 2018.
Ota, H., et al., "Highly deformable liquid-state heterojunction sensors", Nature Communications, 2014, 5:5032.
Paek, J., et al., "Microrobotic tentacles with spiral bending capability based on shape-engineered elastomeric microtubes", Scientific Reports, Jun. 11, 2015, 11 pages.
Paek, J., et al., "Spiraling Soft-Robotic Micro-Tentacles Based on Shape-Engineered, Highly Deformable Elastomeric Microtubes", 19th International Conference on Miniaturized Systems for Chemistry and Life Sciences, Oct. 25-29, 2015, Gyeongju, Korea, 3 pages.
Pan, Shaowu, et al., "Novel Wearable Energy Devices Based on Aligned Carbon Nanotube Fiber Textiles" (2014).
Park, M., et al., "MoS$_2$-Based Tactile Sensor for Electronic Skin Applications", Adv. Mater. 2016, 28, 2556-2562. (Feb. 2016).
Park, S., et al., "Soft, stretchable, fully implantable miniaturized optoelectronic systems for wireless optogenetics", Nat. Biotechnol. Dec. 2015; 33(12): 1280-1286. doi:10.1038/nbt.3415.
Piwek, L., et al., "The Rise of Consumer Health Wearables: Promises and Barriers", PLOS Med 13(2): e1001953. doi:10.1371/journal.pmed.1001953. (Feb. 2, 2016).

(56) References Cited

OTHER PUBLICATIONS

Ramachandran, T.; Vigneswaran, C. Design and Development of Copper Core Conductive Fabrics for Smart Textiles. J. Ind. Text. 2009, 39 (1), 81-93.
Rogers, C. I., et al., "3D printed microfluidic devices with integrated valves", Biomicrofluidics 2015, 9 (1), 016501.
Ryan, J.D., "Machine-Washable PEDOT:PSS Dyed Silk Yarns for Electronic Textiles", ACS Appl. Mater. Interfaces 2017, 9, 9045-9050.
Schmidt, O. G.; Eberl, K., "Nanotechnology: Thin solid films roll up into nanotubes", Nature 2001, 410 (6825), 168-168.
Schwartz, G., et al., "Flexible polymer transistors with high pressure sensitivity for application in electronic skin and health monitoring", Nat. Commun., 4:1859 doi:10.1038/ncomms2832 (2013).
Sharma, B., et al., "Load-Controlled Roll Transfer of Oxide Transistors for Stretchable Electronics", Adv. Mater. 2013, 23, 2024-2032.
Shyamkumar, P., et al., "Wearable Wireless Cardiovascular Monitoring Using Textile-Based Nanosensor and Nanomaterial Systems", Electronics, 2014, 3, 504-520.
Song, S-H., et al., "A rapid and simple fabrication method for 3-dimensional circular microfluidic channel using metal wire removal process", Microfluid Nanofluid (2010) 9: 533-540.
Stoppa, M., et al., "Wearable Electronics and Smart Textiles: A Critical Review", Sensors, 14, 11957-11992, (Jul. 7, 2014).
Supplementary European Search Report for EP Application No. EP 18 76 0838, "Microtube Sensor For Physiological Monitoring" dated Nov. 5, 2020.
Tao, X., et al., "How to Make Reliable, Washable, and Wearable Textronic Devices", Sensors, 17, 673, 16 pages. (Mar. 24, 2017).
Teh, S.-Y., et al., "Droplet microfluidics", Lab Chip 2008, 8 (2), 198-220.
Unger, M. A., et al., "Monolithic Microfabricated Valves and Pumps by Multilayer Soft Lithography", Science 2000, 288 (5463), 113-116.
Wang, K., et al., "High-Performance Two=Ply Yarn Supercapacitors Based on Carbon Nanotubes and Polyaniline Nanowire Arrays", Ad. Mater. 2013, 25, 1494-1498.
Wang, X., et al., "Self-Powered High-Resolution and Pressure-Sensitive Triboelectric Sensor Matrix for Real-Time Tactile Mapping", Adv. Mater. 2016, (Feb. 16, 2016).
Warkiani, M. E., et al., "Slanted spiral microfluidics for the ultrafast, label-free isolation of circulating tumor cells", Lab Chip 2014, 14 (1), 128-137.
Weaver, J. A., et al., "Static control logic for microfluidic devices using pressure-gain valves", Nat Phys 2010, 6 (3), 218-223.
Whitesides, G. M., "The origins and the future of microfluidics", Nature 2006, 442 (7101), 368-373.

Wong, A. D. et al., "Live-Cell Imaging of Invasion and Intravasation in an Artificial Microvessel Platform", Cancer Res. 2014, 74 (17), 4937-4945.
Xi, W., et al., "Soft tubular microfluidics for 2D and 3D applications", PNAS, Oct. 3, 2017, 114(4): 10590-10595.
Xi, W., et al., "Rolled-up Functionalized Nanomembranes as Three-Dimensional Cavities for Single Cell Studies", Nano Lett. 2014, 14 (8), 4197-4204.
Yang, H., et al., "Soft Thermal Sensor with Mechanical Adaptability", Adv. Mater. 2016, 28, 9175-9181. (Aug. 30, 2016).
Yap, L.W., et al., "Soft piezoresistive pressure sensing matrix from copper nanowires composite aerogel", Sci. Bull. (2016) 61(20): 1624-1630. (Jul. 28, 2016).
Yeo, J.C., et al., "Flexible and Stretchable Strain Sensing Actuator for Wearable Soft Robotic Applications", Adv. Mater. Technol. 2016, 1600018, 9 pages. (May 6, 2016).
Yeo, J.C., et al., "Triple-State Liquid-Based Microfluidic Tactile Sensor with High Flexibility, Durability, and Sensitivity", ACS Sens., Mar. 7, 2016, 9 pages.
Yeo, J.C., et al., "Wearable tactile sensor based on flexible microfluidics", Lab Chip, 2016, 16, 3244-3250. (Jul. 7, 2016).
Yildiz, S.K., et al., "Fabricaion and characterisation of highly stretchable elastomeric strain sensors for prosthetic hand applications", Sensors and Actuators A: Physical, 247, 514-521 (2016). (Jul. 2, 2016).
Yu, P.Y., et al., "Flexible Piezoelectric Tactile Sensor Array for Dynamic Three-Axis Force Measurement" Sensors 2016, 16, 819, 15 pages. (Jun. 3, 2016).
Yue Fei, J., et al., "PDMS microchannel fabrication technique based on microwire-molding", Chinese Science Bulletin, Dec. 2008, 53(4): 3928-3936.
Yun, Y.J., et al., "A Novel Method for Applying Reducted Graphene Oxide Directly to Electronic Textiles from Yarns to Fabrics", Adv. Mater. 2013, 25, 5701-5705.
Zervantonakis, I. K., et al., "Three-dimensional microfluidic model for tumor cell intravasation and endothelial barrier function", Proc. Natl. Acad. Sci. USA 2012, 109 (34), 13515-13520.
Zhang, H., et al., "Piezoresistive Sensor with High Elasticity Based on 3D Hybrid Network of Sponge@CNTs@Ag NPs", ACS Appl. Mater. Interfaces 2016, 8, 22374-33281. (Aug. 2, 2016).
Non-Final Office Action for U.S. Appl. No. 16/078,896, "Versatile, Flexible And Biocompatible Elastomeric Microtubes" dated Dec. 24, 2020.
Lee, H., et al., "A graphene-based electrochemical device with thermoresponsive microneedles for diabetes monitoring and therapy", Nat Nano 2016, 11, 566-574.
Notice of Allowance for U.S. Appl. No. 16/078,896 "Versatile, Flexible and Biocompatible Elastomeric Microtubes" dated Jun. 30, 2021.

* cited by examiner

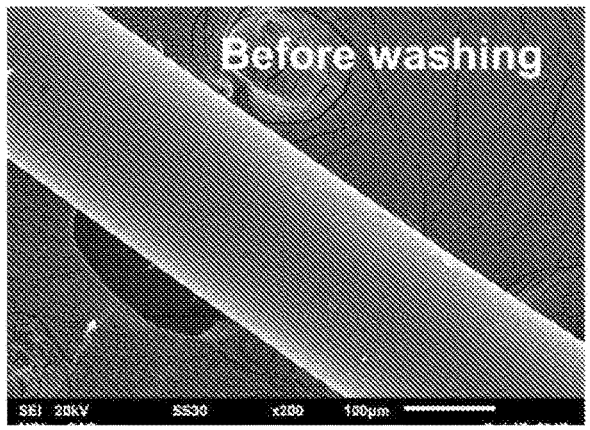
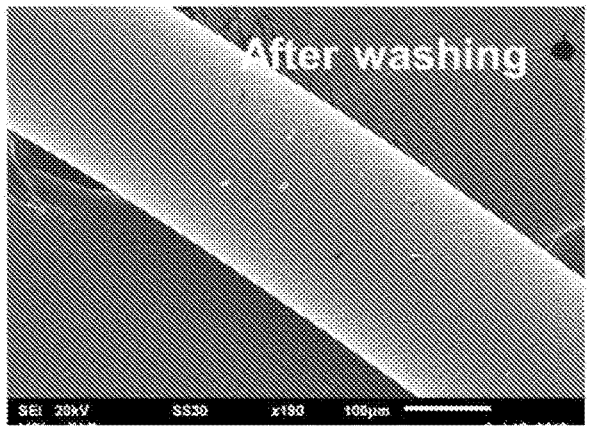
FIG. 11A          FIG. 11B
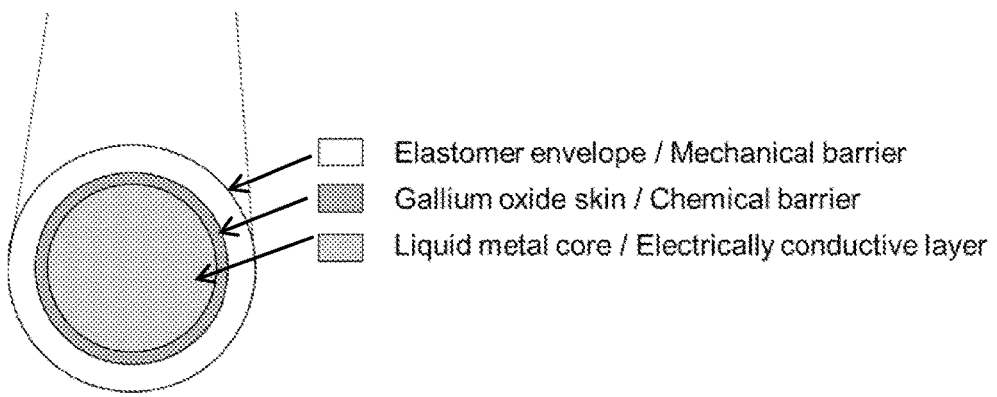
- Elastomer envelope / Mechanical barrier
- Gallium oxide skin / Chemical barrier
- Liquid metal core / Electrically conductive layer
FIG. 12

MICROTUBE SENSOR FOR PHYSIOLOGICAL MONITORING

RELATED APPLICATION(S)

This application is the U.S. National Stage of International Application No. PCT/SG2018/050076, filed Feb. 19, 2018, which designates the U.S., published in English, and claims the benefit of U.S. Provisional Application No. 62/465,002, filed on Feb. 28, 2017. The entire teachings of the above applications are incorporated herein by reference.

BACKGROUND

Recent years have seen significant attention devoted to flexible electronics, leading to tremendous progress in soft and wearable sensors. Compared to rigid sensors, sensors that are flexible, stretchable, and bendable have shown enormous potential in health monitoring, soft robotics, electronics skins, and prosthetics. Elastic mechanical properties are the key factors for wearability and imperceptibility to enable conformal skin contact for in situ monitoring. However, conventional silicon-based devices and many conductive materials are mechanically stiff and brittle. To overcome this, some approaches have deposited conductive layers of carbon nanotubes, nanoparticles, nanowires, and two-dimensional materials, onto stretchable substrates, resulting in an overall mechanical deformability. The composite materials require conventional manufacturing methods, such as transfer printing, electroless deposition or electrodeposition, and screen printing, which typically restrict designs and integration of operational elements in a planar environment. Furthermore, the sensors' complicated structures, in many cases, require more expensive and complex production routes, limiting scalability and reproducibility.

SUMMARY OF THE INVENTION

Described is a flexible, stretchable, soft, and ultrathin wearable tactile sensor that is highly sensitive to mechanical perturbations. The sensor comprises a unique architecture including a liquid-state conductive element core within a soft silicone elastomer microtube. The microtubular sensor can distinguish forces as small as about 5 mN and possesses a high force sensitivity of about 68 $N^{-1}$. The sensor exhibits superior sensing capabilities to detect perturbations from pulsatile air flows and can be applied in continuous and imperceptible real-time monitoring of arterial pulse waves.

Embodiments of the invention have distinctive characteristics that provided benefits and advantages over existing technologies. The microtube sensor possesses a footprint (e.g., outer diameter) of less than about 120 µm. Its tiny footprint is approximately a cross-section of a strand of hair, which is one of the smallest in the existing technologies. This enables users to apply the sensor almost indistinguishably, thereby improving compliance and comfort. Furthermore, the tubular structure allows conformability over 3D curvatures, which cannot be achieved with planar substrates.

In addition, due to the manufacturing techniques used for making the microtube, an ultrathin wall thickness of about 10 µm can be achieved, which is one of the thinnest in the existing technologies. The ultrathin wall thickness enables the sensor to achieve high sensitivity, implying that the sensor does not require additional signal conditioning. This can further reduce the electronics components, increasing the sensor's wearability for the user.

Furthermore, the microtube can be extended to very long lengths up to about 1 meter, which is useful for applications that require a large surface area sensing. Even with longer lengths, the volume of liquid metallic alloy is considerably low, which makes the sensor low-cost and effective.

An embodiment of the microtube sensor of the invention can meet the requirements of highly robust, responsive, sensitive force measurements while maintaining its flexibility, stretchability and wearability. Potential applications of the microtube sensor include:

Microfibers for wearable electronics and smart textiles;

Non-invasive physiological monitoring of pulse pressure or heart rate, such as in wearable healthcare monitoring devices;

Real-time measurements of forces in healthcare applications such as foot pressure;

Prosthetics or artificial skin systems, to improve or regain the tactile perception; and Industrial applications requiring detection of forces in constricted areas, such as manufacturing, packaging and automobile.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1A illustrates preparation of a microtube according to a customized extrusion technique using a metal wire.

FIG. 1B illustrates removal of the metal wire to create a hollow microtube. An optical micrograph reveals the tube of 100 µm in inner diameter with a thickness of 10 µm (left, upper row of FIG. 1B). Liquid eGaIn is injected into the microtube, and an optical image shows eGaIn occupied the lumen within the microtube (right, upper row of FIG. 1B). The microtube filled with eGaIn is sealed at the ends to retain the eGaIn in the lumen of the microtube, and connected to circuitry via cables to complete the sensor device (lower row of FIG. 1B).

FIG. 1C, left and right, are photographs illustrating (left) actual fabricated liquid-based microtubular sensor seen on a fingertip, and (right) size of microtubular sensor in comparison to a strand of hair.

FIG. 1D are optical and SEM images of an example microtubular sensor showing a flexible tube with uniform outer diameter.

FIG. 1E is a micrograph illustrating bendability of the microtubular sensor around a sharp tip with bend radius below 0.2 mm.

FIG. 2A is a schematic illustration of the mechanical deformation of the microtube between two parallel rigid plates. The black arrow indicates the compressive direction.

FIG. 2B illustrates change in the normalized cross-sectional area (solid line) and transmitted light intensity (boxed line) as a function of compressive forces. The insets are optical images of eGaIn filled microtubes with/without compressional loads.

FIG. 2C illustrates results of a numerical analysis showing indentation displacement of the pincher that applies different compressive forces on the microtubes of various elastic moduli, i.e., 5, 10, 15, 20, and 25 MPa. The black dots represent the experimental results.

FIG. 2D illustrates force-induced resistance change (normalized $R/R_0$) with microtubes of constant diameter ratio $d_o/d_i=1.2$ but of different inner diameter, i.e., 50, 100, 150 and 200 μm.

FIG. 3A illustrates an electrical resistance profile of an embodiment of the microtube sensor at 5 mN loading-unloading cycle. The inset shows a schematic of the experimental setup for applying normal load on the sensor.

FIG. 3B illustrates an electrical resistance profile of the microtube sensor over various loads. The inset shows the magnified view of the resistivity changes of the sensor at low pressures.

FIG. 3C illustrates electrical profile of cyclic loadings of over 500 cycles on the microtubular sensor. The inset shows a magnified view of the over 25 cyclical responses of the highlighted region, showing consistency and repeatability.

FIG. 3D illustrates an electrical profile of the sensor at various external loadings, demonstrating the sensor reliability.

FIG. 3E is a schematic illustration showing the airflow generated by an air piston over the sensor in a continuous sweeping motion.

FIG. 3F illustrates electrical impedance profiles of the device when subjected to varying air pressures. The inset shows the persistent resistance increase when the sensor is exposed to continuous air flow.

FIG. 4A is a photograph showing a microtube sensor attached firmly over the brachial artery at the elbow of a human subject. The arrow indicates the position of the sensor.

FIG. 4B illustrates relative electrical resistance change ($\Delta R/R0$) of the sensor of FIG. 4A reflecting the brachial arterial pulse waveform. The P1, P2 and P3 denote three distinct peaks indicative of incident, tidal, and diastolic wave.

FIG. 4C illustrates a sensor recording at the wrist of a human subject over a period of 10 s using an embodiment of the present invention. The inset shows the representative of the wrist arterial pulse waveform.

FIG. 4D illustrates a sensor recording at the wrist after exercise. The inset shows the representative of the wrist arterial pulse waveform, with P1 and P3 peaks.

FIG. 6A is a photo highlighting the STEP-microfiber woven into a fabric glove. The inset shows the magnified view with the arrow pointing at the STEP-microfiber (scale bar represents 15 mm). FIG. 6B is a magnified image showing an ant on top of the STEP-microfiber (scale bar represents 5 mm). FIG. 6C illustrates that the STEP-microfiber can be stretched by more than 150% of its original length (scale bar represents 20 mm).

FIG. 7A illustrates an experimental setup of the electronic textile testing before stretching and after 40% strain. FIG. 7B illustrates the relationship of the normalized electrical resistance ($\Delta R/R_0$) of the STEP-microfiber with strain. Inset shows a magnified view of the $\Delta R/R_0$ up to 40% strain. FIG. 7C illustrates electrical resistance of the STEP-microfiber following washing in a beaker using magnetic stirring bar and temperature>32° C. Inset shows the photograph of the experimental set up. FIG. 7D illustrates electrical resistance of the STEP-microfiber after washing cycles in a front load washing machine.

FIG. 8A is a graph of normalized resistance as a function of pressure for different diameter fibers illustrating force sensing characteristics of the STEP-microfibers. FIG. 8B is a photograph of the microfibers in a cross-stitched network. Intersection points of the microfibers are labelled with A, B, C, and D, respectively. Microfibers are labelled with R1, R2, R3, and R4, respectively. FIG. 8C illustrates electrical signals of the respective microfibers when the following positions on the fabric were pressed on: points A, B, C, and D, respectively. FIG. 8D illustrates electrical signals of the respective microfibers with different swiping actions.

FIG. 9A illustrates a user measuring the carotid pulse near the neck and recorded normalized electrical resistance ($\Delta R/R_0$) indicating the pulse waveforms at the corresponding location. FIG. 9B illustrates a user measuring the brachial pulse near the elbow pit and a graph of $\Delta R/R_0$ indicating the pulse waveforms at the corresponding location. FIG. 9C illustrates a user measuring the radial pulse near the wrist and a graph of $\Delta R/R_0$ indicating the pulse waveform at the corresponding location. FIG. 9D illustrates a user measuring the dorsalis pedis pulse near the foot instep and a graph of $\Delta R/R_0$ indicating the pulse waveform at the corresponding location.

FIG. 10A illustrates a conductive microfiber woven on a stretchable bandage. FIG. 10B is a graph of normalized resistance ($\Delta R/R_0$) indicating sustained increase in resistance levels of the bandage of FIG. 10A under different tension conditions. FIG. 10C is a graph of electrical output of the conductive microfiber representing repeated rapid tension and release. FIG. 10D illustrates the STEP-microfibers (R1, R2) woven into a sock. FIG. 10E is a graph of electrical output of the microfibers (R1, R2) showing the gait cycle (i.e., heel strike, mid stance, toe off) during locomotion using a sock as illustrated in FIG. 10D.

FIGS. 11A-11B illustrate washability of the STEP-microfiber. A comparison of SEM images showing the STEP-microfiber before (FIG. 11A) and after (FIG. 11B) washing indicates no obvious damage to the functionalized microfiber.

FIG. 12 is a schematic illustration showing a STEP-microfiber composite. A silicone elastomer layer forms a mechanical barrier, and a gallium oxide skin layer forms a chemical barrier.

FIG. 13A is a schematic illustration that shows the STEP-microfiber constricts due to tension. FIG. 13B is a graph illustrating that normalized resistance increases nonlinearly with increasing tensile strain. FIG. 13C is a graph illustrating that sensitivity increases linearly with increasing tensile strain.

FIG. 14A is a schematic illustration shows the STEP-microfiber constricts due to compression. FIG. 14B is a graph illustrating that normalized resistance increases nonlinearly with increasing normalized pressure, when $\alpha=0.1$. FIG. 14C is a graph illustrating that sensitivity increases nonlinearly with increasing normalized pressure, when $\alpha=0.1$.

DETAILED DESCRIPTION OF THE INVENTION

Figures 1A, 1B, 1C, 1D, 1E:
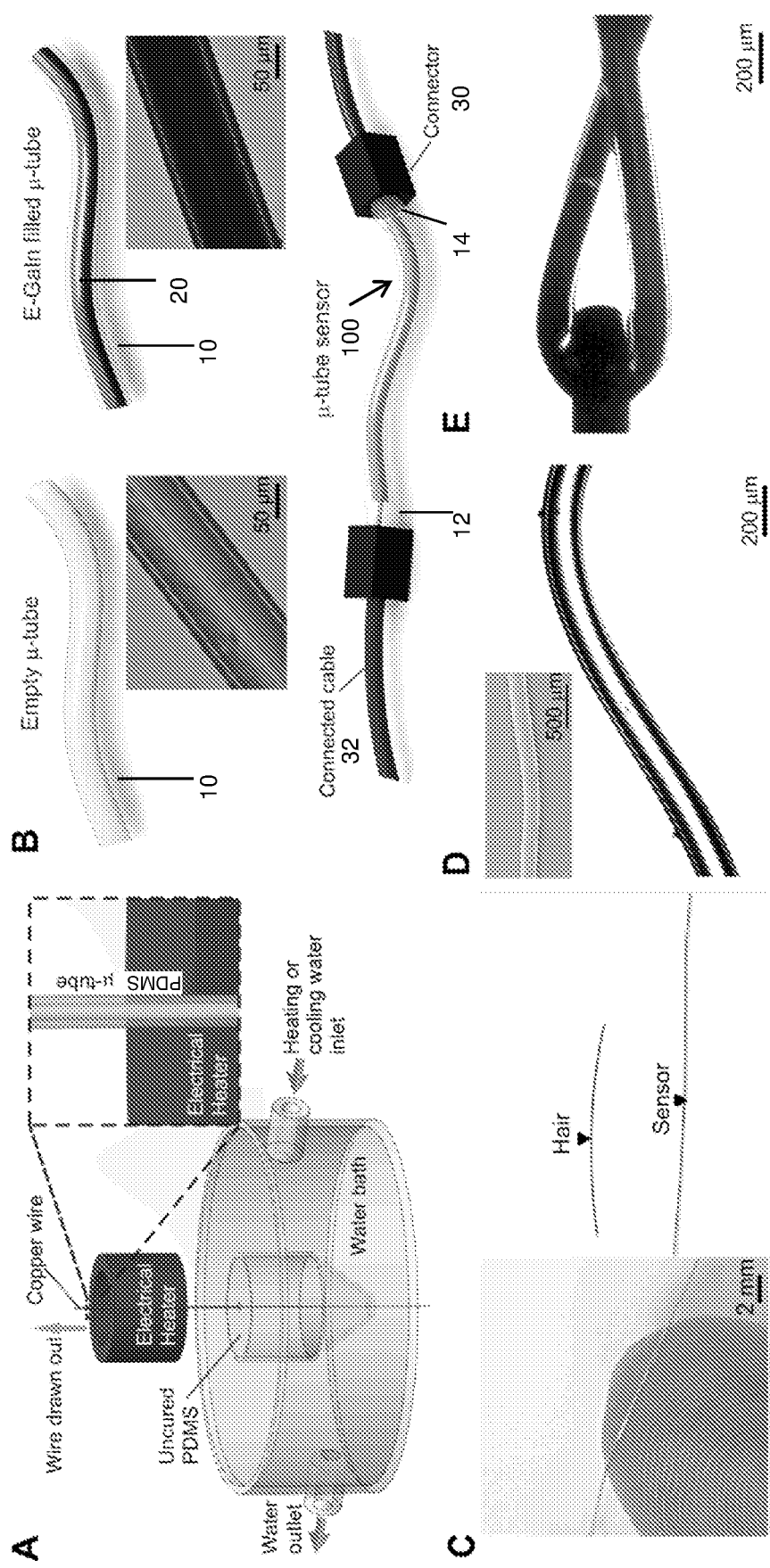
FIGS. 1A-1E illustrate a process of fabricating a liquid-based microtubular sensor and a resulting embodiment of a highly sensitive microtubular tactile sensor.

A description of example embodiments of the invention follows.

Definitions

The term "microtube" as used herein means a tube having an outer diameter in the micrometer range, e.g., between about 1 micrometer and about 999 micrometers.

The term "flexible" as used herein means capable of bending easily without breaking.

The term "polymer" as used herein means a substance that has a molecular structure consisting predominantly or entirely of a large number of similar units bonded together, e.g., many synthetic organic materials used as plastics and resins. The polymer will have at least one of the following properties: flexibility, stretchability, softness and biocompatibility. Examples of polymers include but are not limited to silicone elastomer, ultraviolet sensitive polymer, polyurethane, polyimide, conductive polymer, conductive rubber, thermoplastic and thermoset polymer.

The term "silicone elastomer" as used herein means an elastomer, e.g., a rubber-like material, composed of silicone containing silicon together with carbon, hydrogen, and oxygen. Examples of silicone elastomers include but are not limited to polydimethylsiloxane (PDMS), phenyl-vinyl silicone, methyl-siloxane, fluoro-siloxane or platinum cured silicone rubber.

The term "liquid-state conductive element" as used herein means an element that is a liquid at room temperature and that is conductive to electrical current. Examples include but are not limited to liquid metallic alloys, such as Galinstan™ (eutectic gallium-indium-tin) and eutectic gallium-indium (eGaIn). Other examples include conductive elements, such as carbon nanotubes, silver nanowires, metallic ink and graphene.

The term "electrical resistance" as used herein means an electrical quantity that measures how a device or material reduces the electric current flow through it. The electrical resistance of an electrical conductor is a measure of the difficulty of passing an electric current through that conductor. The resistance explains the relationship between voltage (amount of electrical pressure) and the current (flow of electricity), and is measured in units of ohms ($\Omega$).

The term "force-induced deformation" as used herein means a deformation of a material consequent to or in reaction to application of a force to the material.

The term "ultrathin" as used herein means having a thickness of about 10 μm to about 40 μm, and may be used to describe the thickness of a wall of a microtube as well as the cross-sectional diameter of the microsensor.

A "fabric" as used herein means a material, such as a textile, made through weaving, knitting, spreading, crocheting, or bonding that can be used in production of further goods (garments, etc.).

A "microfiber" as used herein means a fiber having an outer diameter in the micrometer range, e.g., between about 1 micrometer and about 999 micrometers.

All numeric values herein can be modified by the term "about," whether or not explicitly indicated. The term "about" generally refers to a range of numbers that one of skill in the art would consider equivalent to the recited value (i.e., having the same function or result). In some versions the term "about" refers to ±10% of the stated value, in other versions the term "about" refers to ±2% of the stated value.

Microtube Sensor

The invention generally relates to a microtube sensor and associated methods for making a microtube sensor and for sensing force.

A microtube sensor according to an embodiment of present invention includes a flexible microtube comprising a polymer and defining a lumen. The flexible microtube has at least one of (i) an inner diameter of about 10 μm to about 400 μm and a variable outer diameter, and (ii) a wall surrounding the lumen, the wall having a thickness of about 10 μm to about 550 μm. The sensor further includes a liquid-state conductive element within the lumen of the flexible microtube and closed ends to retain the liquid-state conductive element in the lumen. The microtube sensor has the property that a change in electrical resistance of the liquid-state conductive element is indicative of a force-induced deformation of the flexible microtube.

The polymer can be a silicone elastomer, an ultraviolet sensitive polymer, polyurethane, polyimide, conductive polymer, conductive rubber, thermoset or a thermoplastic polymer. The silicone elastomer can be, for example, polydimethylsiloxane, phenyl-vinyl silicone, methyl-siloxane or fluoro-siloxane. The ultraviolet sensitive polymer can be MYpolymer® (a fluorinated resin with acrylate/methacrylate groups produced by MY Polymers Ltd.), styrene-acrylate-containing polymer, polyacrylate polyalkoxy silane, a positive photoresist (e.g., diazonaphthoquinone-based positive photoresist) or a negative photoresist (e.g., epoxy-based negative photoresist).

The liquid-state conductive element can be a liquid metallic alloy, such as Galinstan™ (eutectic gallium-indium-tin) or eutectic gallium-indium (eGaIn). Other suitable liquid-state conductive elements can be conductive liquids, such as ionic solutions, metallic ink, conductive greases or conductive hydrogels. Yet other suitable conductive elements can be metallic nanoparticles or carbon-based materials suspended in liquid solution. Microtube sensors using these conductive elements can be fabricated using the process described below for eGaIn.

The flexible microtube can have an inner diameter of about 10 μm to about 400 μm, preferably about 50 μm to about 200 μm, and a variable outer diameter. A ratio of the outer diameter to the inner diameter can be in the range of about 1.05 to about 111, and preferably is about 1.2. The length of the microtube can be about 1 m or less and at least about 200 μm. The microtube can have a wall surrounding the lumen, the wall being of the same material as the microtube. The wall can have a thickness of about 10 μm to about 550 μm, preferably about 10 μm to about 40 μm. The outer diameter can vary in size depending upon the thickness of the wall. The outer diameter is controllable by varying certain parameters during the fabrication process, such as pulling speed of the metal wire used in the process and the viscosity and surface tension of the polymer (e.g., liquid PDMS), as further described in U.S. Provisional Application No. 62/302,919 filed on Mar. 3, 2016, entitled "Versatile, Flexible And Biocompatible Elastomeric Microtubes," the entire teachings of which are incorporated herein in their entirety. The inner diameter is typically determined by the cross section (e.g., outer diameter) of the metal wire.

The force sensitivity of the microtube sensor can be about 2.8 $N^{-1}$ to about 68 $N^{-1}$ for static force loads from about 5 mN to about 900 mN.

The microtube can have a circular, elliptical, rectangular, square, triangular, star, non-circular, or irregular cross-sectional shape.

Connectors (e.g., wires) can be provided at the ends of the microtube and in electrical contact with the liquid-state conductive element, to measure electrical resistance of the liquid-state conductive element. The ends of the microtube can be closed, for example, by sealing the ends using the same material as is used for fabricating the microtube, such as PDMS or other suitable material, or by crimping the ends of the microtube, or by attaching caps to the ends of the microtube.

An ultrathin microtube resistive sensor of the invention is soft, flexible, stretchable, and simple to manufacture. The microtube facilitates the deployment of liquid metallic alloy eGaIn that serves as a thin flexible conduit with excellent electrical conductivity and mechanical deformability. Specifically, by considering the radius and thickness of the microtube, an ultrasensitive liquid-based tactile sensor with high flexibility and durability can be realized. The self-sustaining fiber-like shape of the sensor is entirely conformal to human interfaces due to its ability to twist around three-dimensional curvatures and objects. In addition, its tiny footprint of about 100 µm to about 200 µm, preferably about 120 µm, in outer diameter makes it almost imperceptible when worn on bare skin. Embodiments of the present invention can be used in imperceptible epidermal healthcare diagnostics and monitoring platforms.

Embodiments of the invention can include one or more of the following features, listed in Table 1, which can provide the associated benefits or advantages.

TABLE 1

| Feature | Benefit/Advantage |
| --- | --- |
| Flexible | Microtube sensor is flexible and can be easily bent to conform to curvatures. |
| Imperceptible | Microtube sensor is almost invisible to the user, improving his ease of use and wearability. |
| Soft | Microtube sensor is as soft as skin, allowing compliance and sensitivity to mechanical forces |
| Ultrathin wall thickness | Allows highly responsive measurements |
| Liquid-based sensing element | Allows highly responsive and robust measurements |

Manufacturing Method and Performance Metrics

In another aspect, the disclosure pertains to a method of making a microtube sensor. The method comprises providing a flexible microtube comprising a polymer and defining a lumen, the flexible microtube having at least one of (i) an inner diameter of about 10 µm to about 400 µm and a variable outer diameter, and (ii) a wall surrounding the lumen, the wall having a thickness of about 10 µm to about 550 µm; injecting a liquid-state conductive element into the lumen of the flexible microtube; and closing ends of the flexible microtube to retain the liquid-state conductive element in the lumen, to thereby make a microtube sensor that has the property that a change in electrical resistance of the liquid-state conductive element is indicative of a force-induced deformation of the flexible microtube.

FIGS. 1A-1D schematically illustrate the fabrication process of the microtubular tactile sensor 100. As shown in FIG. 1A, the tubular silicone elastomer 10 was first prepared using a customized extrusion technique. A detailed description of the technique is provided, for example, in U.S. Provisional Application No. 62/302,919 filed on Mar. 3, 2016, entitled "Versatile, Flexible And Biocompatible Elastomeric Microtubes," the entire teachings of which are incorporated herein in their entirety. Briefly, uncured polydimethylsiloxane (PDMS) base and curing agent were mixed in a container. A metal filament was drawn vertically from within the container. Due to the viscosity and surface tension of the PDMS, a uniform thin layer of PDMS was formed around the metal wire (e.g., copper or tungsten wire) as it was drawn above the solution. To further improve its wettability, hot water (~98° C.) was added to the water bath to allow partial curing of PDMS and ice-cold water was used to maintain the PDMS viscosity. Next, a cylindrical electrical heating unit (~150° C.) was positioned above the container to cure the PDMS on the filament entirely. Once it was fully cured, the metal wire was removed to form the hollow tubular structure 10 (FIG. 1B). The microtube tactile sensor measured with an internal diameter of 100 µm and the outer diameter of 120 µm. Such a sensor, having an internal diameter of 100 µm with a wall thickness of 10 µm, is five times smaller than the smallest sensor reported in the literature at present. The inner diameter of the microtube could also be varied with different diameters of metal wire. The microtube structure 10 was then filled with eGaIn 20, closed at both ends 12, 14, and further connected with connectors 30 and electrical cables 32, completing the overall tactile sensor 100 (FIG. 1B). The length of the tactile sensor could be easily customized to different lengths up to several tens of centimeters for various applications. The diameter of the tactile microtubular sensor is comparable to a strand of hair and is hardly perceptible at the fingertip (FIG. 1C). Owing to the facile fabrication method, the entire tube is consistently uniform in diameter, and flexible (FIG. 1D). Furthermore, the microtube is very thin and soft (FIGS. 1B, 1C and 1D), and could be bent over a sharp tip with a bend radius of approximately 200 µm, indicating its conformability of the microtubular sensor over tight curvatures (FIG. 1E). Overall, the microtubular sensor is highly bendable, flexible, twistable, and stretchable. Importantly, the combination of an ultrathin wall thickness and low modulus allows for an efficient mechanotransduction of the forces to the liquid metal core, hence extending this capability to measure physiological signals.

The sensing mechanism of the microtubular sensor is based on the deformation when exposed to external mechanical forces. As the sensor is compressed, the microtube flattens and constricts, and the cross-sectional area decreases. Subsequently, the reduced volume and displacement of the conductive eGaIn metallic alloy at compressed region will cause an increase in its electrical resistance. Assuming an incompressible, elastic system, the resistance of the sensor R can be expressed as $$dR = \frac{\rho \cdot dl}{A(l)} \tag{1}$$

where ρ is the electrical resistivity of the liquid metallic alloy, dl is per unit length, and A(l) is the function of the cross-sectional area over length l. Here, the rigid plates can be assumed to compress the tube into an obround shape. Therefore the equation may be further simplified into $$dR = \frac{4\rho \cdot dl}{\pi(d_i^2 - U^2)} \tag{2}$$

where $d_i$ is the inner diameter of the tube, and U is the function of deformation over length l. It is worthwhile to note that U depends on dynamic extrinsic force F(t), intrinsic material property, i.e., Young's modulus, E, and geometrical parameters, such as inner and outer diameters, $d_i$ and $d_o$.[1] Apparently, a small deformation may be translated to a large resistance change, highlighting the sensitivity of the sensor.

Figures 2A, 2B, 2C, 2D:
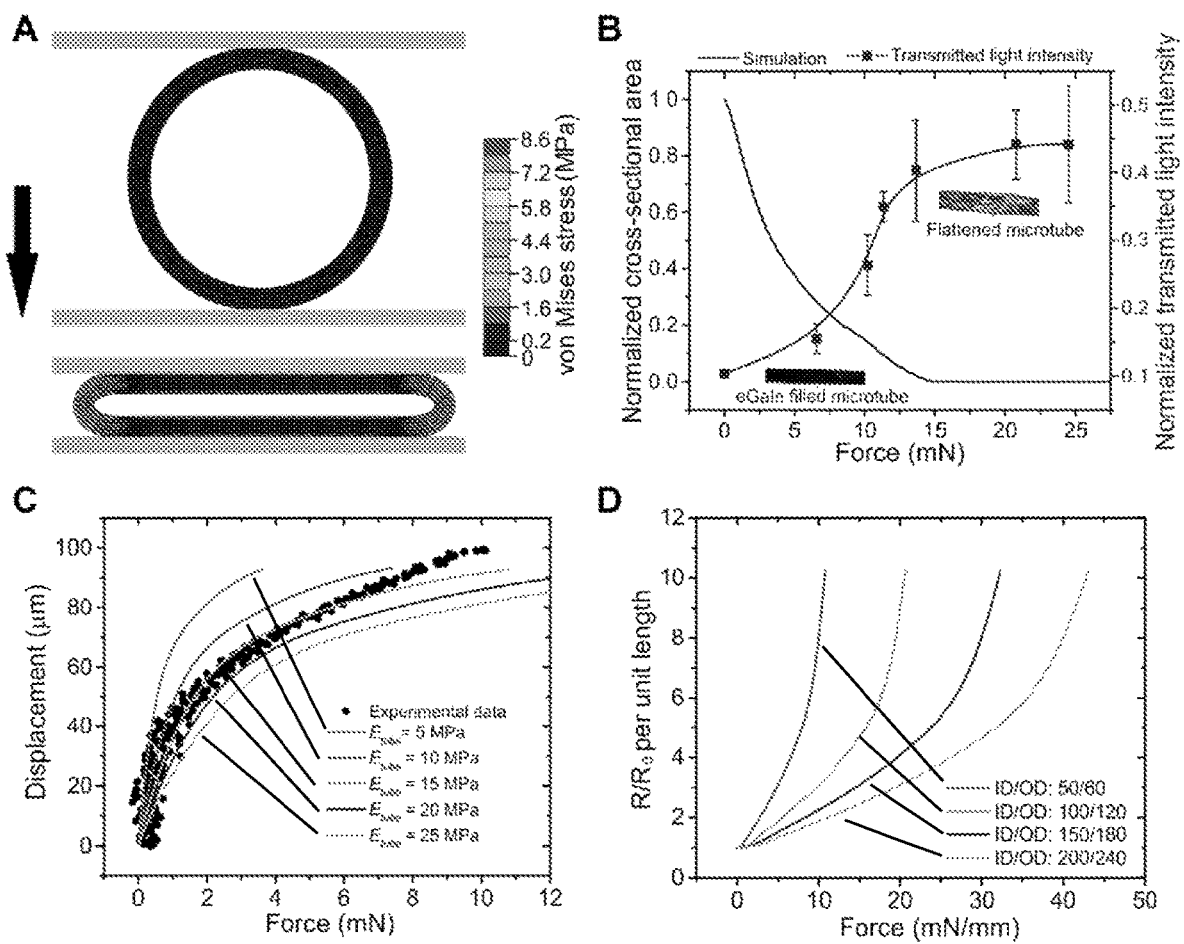
FIGS. 2A-2D illustrate finite element modeling and experimental data of the mechanical deformation of the microtubular sensor upon different loads.

To study the compression of the microtube, finite element analysis was used to simulate the cross-sectional deformation between two rigid, flat plates as shown in FIG. 2A. First, static compression to 95% of the inner diameter was performed. FIG. 2A shows the cross-sectional deformation of the microtube. Notably, the highest stress regions occurred at the intersection of the transverse plane and inner surface of the microtube, where von Mises stress measured 8.44 MPa. Even so, the stresses were much lower than the ultimate compression strength of PDMS reported in the literature,[2] further implying its structural integrity and robustness.

Furthermore, the change in the cross-sectional area of the lumen under dynamic compressive loading was measured. FIG. 2B shows the cross-sectional area as a function of the compressive forces. The simulation results indicated that the microtube could be deformed by almost 80% decrease in the cross-sectional area under external forces as small as 8 mN. To validate the model, the transmitted light intensity was measured through the compressed microtubular sensor. It was discovered that as the microtube was compressed, the opaque eGaIn filled microtube gradually became translucent, and the transmitted light intensity plateaued under a compressional force of ~13 mN (FIG. 2B). This observation is consistent with the simulation, which presents a decreasing trend of the tubular cross-sectional area and indicates a flattened microtube at force≥15 mN. Taken together, these findings further highlight the excellent deformability of the microtube.

The compression by parallel rigid plates induces both tensile and compressive stresses within the microtube. A different elastic moduli (i.e., $E_{tube}$=5, 10, 15, 20, and 25 MPa) was applied to the model and compared the results with the experimentally measured indentation displacement vs. force plot (FIG. 2C). By doing so, the equivalent Young's modulus of $E_{tube}$=15 MPa was determined. The high Young's modulus is due to the incompressibility of the liquid metal within the microtube, which provided extra pressure when the sensor was transversely compressed. To determine the optimal tubular geometry for pressure sensing, the deformation profile of microtubes with different $d_i$ and $d_o$ was simulated under compressive forces. The thickness of the PDMS film, $h=(d_o-d_i)/2$, which attached to the metal filament, is proportional to the thread diameter, $d_i$, and the intrinsic capillary number, Ca, of the liquid PDMS:

$$h \propto d_i Ca^{2/3} \tag{3}$$

where Ca is relevant to the viscous forces and surface tension.[3] The fabrication conditions were optimized to produce microtubes with h as thin as 10 μm with a $d_o/d_i$ ratio of 1.2. The force-induced resistance change, $R/R_0$, was computed as a function of the compressive forces with the fixed ratio of 1.2 as shown in FIG. 2D. As expected, the sensitivity of the microtubes with different inner diameters is increased with reducing $d_i$ and h. However, when the inner diameter is reduced to 50 μm, the liquid surface tension created beading of the PDMS,[4] leading to unsmooth surfaces. Therefore, consistently smooth microtubes of $d_o/d_i$=120/100 μm could be fabricated for the implementation of the microtube sensor.

Figures 3A, 3B, 3C, 3D, 3E, 3F:
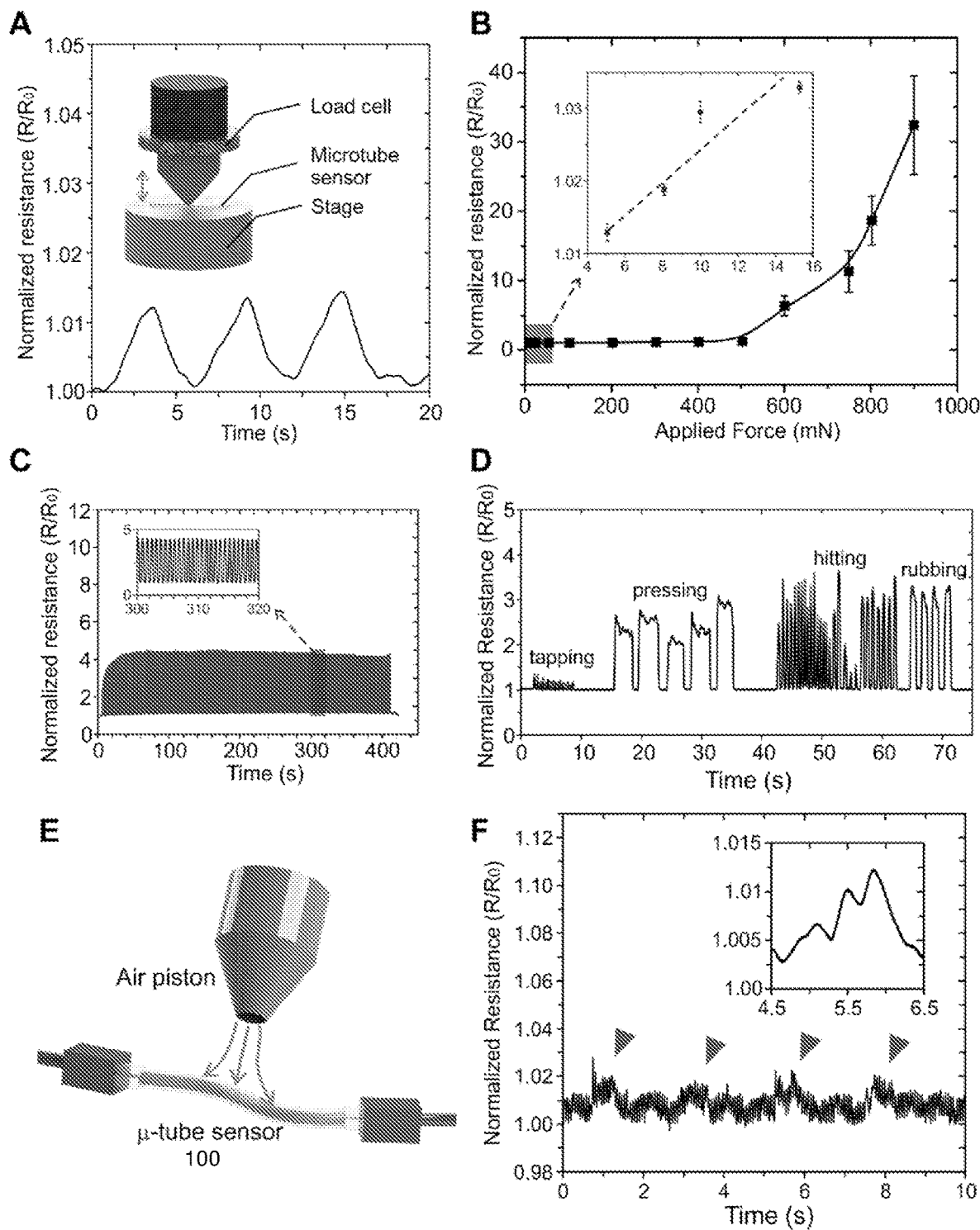
FIGS. 3A-3F illustrate pressure sensing and reliability performance of the microtubular sensor.

Output characteristics at different mechanical loads are illustrated in FIGS. 3A-3F. First, the pressure sensing and reliability performance of the microtubular sensor was characterized in response to both static and dynamic mechanical forces. Static loads from 5 mN up to 900 mN were performed using a universal pressure machine (FIG. 3A, inset). As shown in FIG. 3A, the sensor was placed on a lower stage of the machine and an upper stage, including a load cell to measure force, applied forces to the sensors. Notably, forces as small as 5 mN could be distinguished. Even at small forces, the sensor demonstrated a pressure sensitivity of about 2.8 $N^{-1}$ (FIG. 3B, inset). When the tube was further compressed with higher forces, the pressure sensitivity increased significantly to approximately 68 $N^{-1}$. Compared with other reported flexible tactile sensors,[11-15] the microtube sensor of the invention possesses a higher sensitivity by about three orders of magnitude. This was because of the high lumen constriction resulting in a thin layer of conductive liquid metal, which increased the electrical resistance dramatically. In addition, the sensor resistance resumed its baseline once was released from the compression, indicating the excellent elasticity of the microtube in shape-reconfigurability. Taken as a whole, it was observed that the sensor was very responsive to external pressures, and demonstrated negligible electrical hysteresis. Indeed, unlike resistive nanocomposites that suffered from endemic low recovery and mechanical hysteresis,[5] the microtubular sensor responded to force changes within 5 ms at a frequency up to 75 Hz.

To test its durability, the sensor was subjected to continuous cyclical loading by indenting the sensor repeatedly at ~1.25 Hz (FIG. 3C). Here, it was observed that the electrical profile of the sensor remained consistent even after 500 cycles. The inset further shows the magnified view of 25 cycles of the sensor response during the durability testing. Notably, the base and peak values were highly consistent, highlighting its precision and high fidelity. Other than cyclical loading, the sensor was subjected to random low and high-pressure loads, including gentle, brief taps, continuous oppression and repeated transient high force loadings. FIG. 3D shows the sensor response after the stress test, where the sensor was highly responsive to various pressure loads. Moreover, the sensor maintained a highly consistent baseline throughout the repeated loading-unloading cycles, further demonstrating the robustness and adaptability of the sensor to extreme loadings. To further prove the sensitivity of the microtubular sensor, a non-contact force was applied on the sensor. FIG. 3E illustrates the detection of air flow generated by an air piston when it moved in a sweeping motion over the microtube sensor 100. FIG. 3F denotes the sensor response where notable peaks were observed when the air was blown over the sensor. Furthermore, sustained air flow triggered a continuous increase in resistance but returned to baseline once the air flow stopped (inset of FIG. 3F). Overall, this demonstrates the ability of the sensor to detect persistent pressure changes and could be applied to a variety of applications, such as turbulent flow and vibrational alternations.

By utilizing fluid displacement to detect micro-deformations, a high sensitivity of >68 N$^{-1}$ was achieved. Furthermore, the microtubular sensor has demonstrated to withstand extreme mechanical load applications without compromising its electrical output stability, conductive liquid confinement, and overall integrity. Accordingly, dynamic forces involving pressing, bending, stretching, twisting, can be resolved using the sensitive sensor.

Sensing Methods and Applications

Based on their properties, such as physical dimensions of the flexible microtube and type of liquid-state conductive element as discussed above, the microtube sensors of the invention can be employed in methods for sensing force. According to an embodiment of the present invention, a method for sensing force comprises exposing the microtube sensor to a mechanical force and measuring a change in electrical resistance of the liquid-state conductive element within the lumen of the flexible microtube in response to the mechanical force. The change in electrical resistance of the liquid-state conductive element is indicative of a force-induced deformation of the flexible microtube.

Exposing the microtube sensor to a mechanical force can include, for example, subjecting the sensor to a contact force, such as a compression force, extension force, twisting force or combination thereof, or a non-contact force, such as airflow pressure or other non-contact perturbation. In response to the mechanical force, the microtube sensor may bend, twist, stretch, or otherwise deform. The mechanical force can be static or dynamic.

The method of sensing can include using the measured change in the electrical resistance to monitor a physiological parameter, which can be at least one of pulse pressure, blood pressure, heart rate, foot pressure, tactile force and tremor.

Figures 4A, 4B, 4C, 4D:
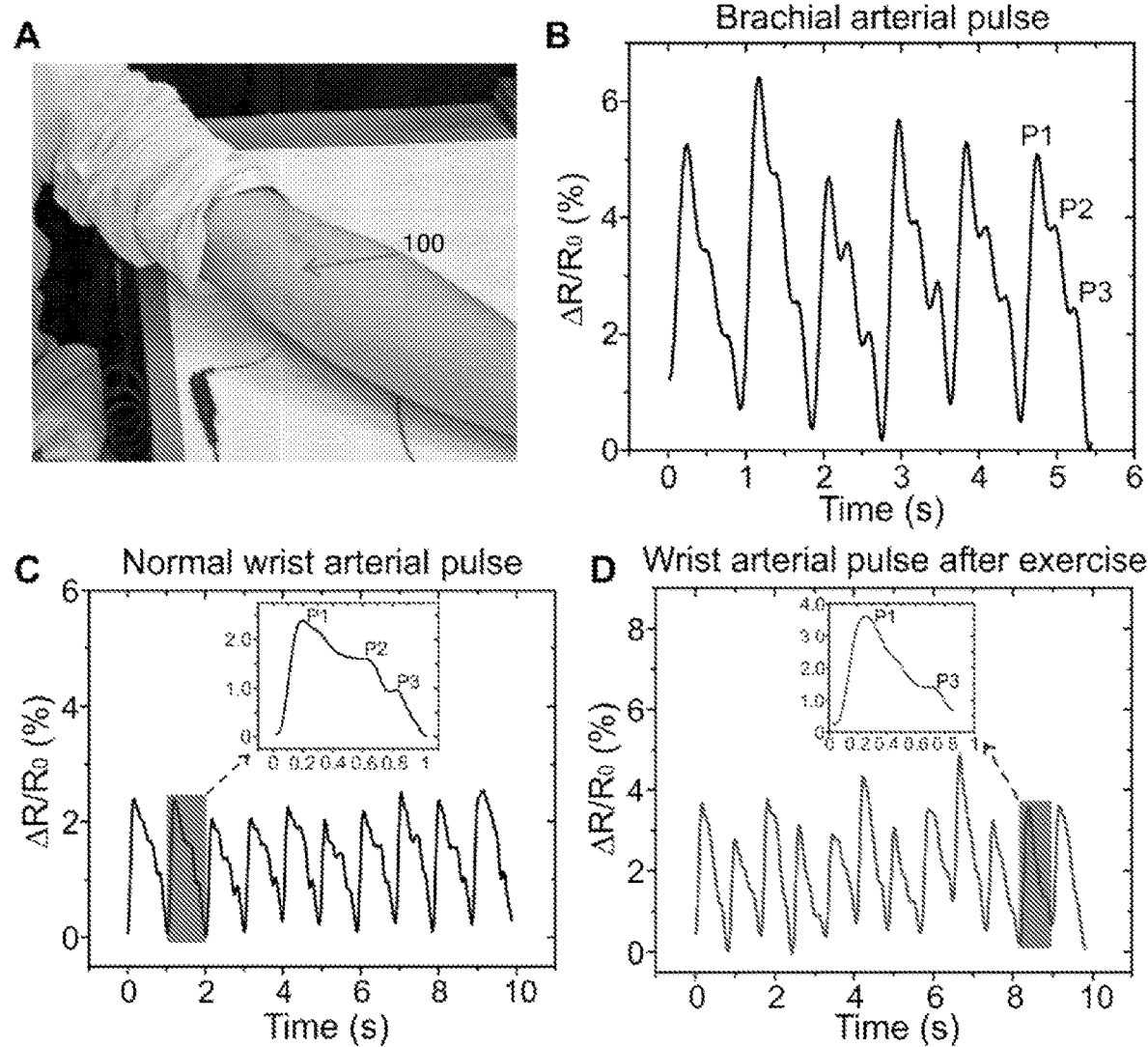
FIGS. 4A-4D illustrate applications of embodiments of the liquid-based microtubular sensor.

The recording of subtle physiological signals is highly desirable for health monitoring. When attached to the bare skin, the sensor 100 could be used to detect subtle force signals caused by physiological pressure flows, such as the brachial or the radial artery pulse (FIG. 4A). Notably, the brachial pulse profile could be distinctly observed with high fidelity through the readout in the resistive variation of the sensor, as shown in FIG. 4B. Specifically, the pulse wave contains three distinct peaks, representative of the incident wave (P1), tidal wave (P2), and diastolic wave (P3). Here, the augmentation index, measuring the ratio of P2 and P1, and the time difference between P1 and P2 could be utilized as a measure of arterial stiffness and age.[8] The sensor was attached to the wrist to measure radial artery pulse. FIG. 4C shows the distinct pulse waveform with similar peaks, demonstrating its versatility in measuring different sites. In fact, in comparison to the brachial pulse, the tidal wave is further from the incident wave, which is indicative of a radial pulse waveform. Subsequently, the radial pulse waveforms after exercise were measured. FIG. 4D shows the pulse waveform in the post-exercise state. Here, it was observed that the pulse rate was higher (75 beats/min compared to 60 beats/min in the resting state). Moreover, in the post-exercise pulse waveform, it was observed that peak pressures are increased by a factor of ~1.5, indicating a higher blood pressure, which is normal after exercise. The tidal wave was also less prominent in the post-exercise state, which could be due to the effect of artery enlarging or altered ventricular ejection as a result of increased demand for oxygenated blood.[6, 7] Importantly, the dynamic pulse profile obtained by the sensor noninvasively was well comparable to that acquired by invasive catheterization methods.[9] Thus, an embodiment of the microtube sensor is capable of measuring and resolving hemodynamic parameters real-time and in almost imperceptible conditions, allowing continuous and unobtrusive monitoring of physiological signals for abnormalities and early disease detection.

Figure 5:
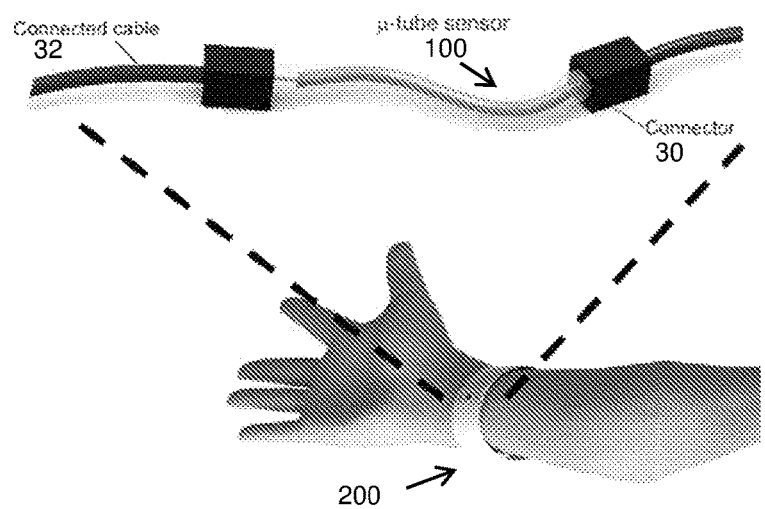
FIG. 5 is a schematic illustration of a wearable microtubular tactile sensor device for real-time physiological pulse monitoring.

The microtube sensor can be included in a wearable device for real-time physiological monitoring, such as the wrist-worn pulse monitoring device 200 illustrated in FIG. 5. The wearable device 200 can include the sensor 100, a power supply and electronic circuitry to drive the sensor, e.g., to measure changes in electrical resistance, current, capacitance, voltage of the liquid-state conductive element.

Example 1—Finite Element Analysis

Finite element modeling of the microtube tactile sensors was performed using ABAQUS CAE for both 2D plane strain and 3D analyses, depending on the geometry of the top pitch (i.e., the crosshead compressing the microtube). Due to symmetry, half and quarter models were established for 2D plane strain and 3D analyses, respectively. General static analysis mode was selected with hard and frictionless contact established between the top pitch and the top half outer surface of the microtube, bottom plate and lower half outer surface of the microtube, as well as the microtube inner surface. Hybrid and linear elements with reduced integration were used for contact analysis. The tube wall was divided into 6 layers in the large stress regions near the mid-plane, and 4 layers in the other regions. Flexible polydimethylsiloxane (PDMS) was assumed to be elastic,[10] and Poisson's ratio was chosen to be 0.49.

Example 2—Device Design and Fabrication

To create the microtube, a metal filament (e.g., wire) was first immersed vertically into a freshly mixed PDMS base and curing agent, 10:1 (w/w) (e.g., mixture of Sylgard 184 silicone elastomer base and Sylgard 184 silicone elastomer curing agent, 10:1 by weight). The metal filament was drawn out of the PDMS pool using a rotary motor at a velocity of 2 to 4 mm/s. Simultaneously, hot water of ~100° C. was added to the surrounding PDMS pool to initiate PDMS curing. When the metal wire was drawn out vertically above the liquid level, it was further cured by hot air at ~95° C. in a cylindrical heating unit. To maintain the optimal viscosity of the PDMS for even coating around the metal filament, cold water would be added into the PDMS pool surroundings to prolong curing time. Next, the metal wire was peeled off during a sonication process in acetone solution which would wash off unreacted elastomer curing agent and caused slight swelling in the polymer—loosening the PDMS-metal contact. The detached PDMS microtube was then baked in an oven to remove any acetone remnant. Subsequently, eGaIn was injected into the microtube using a 1 mL syringe. Wires were then inserted into the hollow microtube and sealed using uncured PDMS, which closed the end of the microtube to retain the eGaIn within. The entire device is brought into the oven at 75° C. for 2 hours to obtain the final product.

Example 3—Pressure Sensing, Durability and Mechanical Forces Differentiation The liquid-based microtube tactile sensor was subjected to compressive ramp-hold-release loads starting from 10 mN to 100 mN using a universal load machine (5848 MicroTester, Instron, Norwood, Mass.), as schematically illustrated in FIG. 3A. The ramp and release rates were set at 5 mm/min. The electrical response of the tactile sensor upon different load applications was continuously monitored and recorded using a customized data logging microprocessor at 20 Hz.

Example 4—Air Flow Sensing and Pulse Sensing

To validate the capability of the microtubular sensor to measure air flow sensing, an air piston was used, an example of which is illustrated in FIG. 3E. The air cylinder was activated over the sensor at approximately 5 mm away briefly. Air flow pressures of about 50 kPa to 100 kPa were applied to show its ability to measure and quantify varying pressures. Electrical signals obtained were post processed using MATLAB bandwidth frequency filter ($2^{nd}$ order with a cutoff frequency of 0.25 Hz).

For pulse pressure sensing, the microtubular sensor was placed over the skin of the forearm of a subject at positions proximally to the elbow and at the wrist (see also FIG. 4A). The subject was requested to sit still for a few seconds and electrical signals were recorded using PXIe 4081 (National Instruments, Austin, Tex.). The electrical signals were further processed using the same MATLAB filter as for air flow sensing, and pulse rate was calculated by counting the period of each waveform.

Highly Stretchable, Weavable and Washable Piezoresistive Microfiber

A key challenge in electronic textiles is to develop an intrinsically conductive thread of sufficient robustness and sensitivity. Described here is an elastomeric functionalized microfiber suitable for smart textile and wearable electronics. Unlike conventional conductive threads, the microfiber is highly flexible and stretchable, and possesses excellent piezoresistive characteristics. The microfiber is functionalized by enclosing a conductive liquid metallic alloy of low viscosity within the elastomeric microtube, thereby forming a microtube sensor. Embodiments are also referred to herein as Stretchable Tubular Elastic Piezoresistive (STEP) microfibers. In an embodiment, the microtube sensor allows shape reconfigurability and robustness, while maintaining an excellent electrical conductivity of 3.27±0.08 MS/m. By producing STEP microfibers the size of cotton threads, a plurality of piezoresistive microfibers can be woven seamlessly into a fabric to determine force location and directionality. The conductive microfibers can be woven into a fabric substrate, such as a glove, and used to obtain physiological measurements from the wrist, elbow pit, neck, and foot instep. Importantly, the elastomeric layer protects the sensing element from degradation. Experiments show that the microfibers remain functional even after repeated machine washing. These advantages highlight the unique propositions of such wearable electronics for flexible display, electronic textile, soft robotics, and consumer healthcare applications.

A STEP-microfiber is presented that is soft, flexible, stretchable, and washable. Electrical functionality is achieved by depositing a non-viscous liquid metallic alloy, eutectic Gallium Iridium (eGaIn), into an elastomeric microtubular structure. The fabrication process is similar to the microtube fabrication process described above with reference to FIGS. 1A-1D. The STEP-microfibers may be woven into a fabric to produce a fully functional wearable electronics to sense force, position, and directionality, as further described below. To demonstrate its robustness and durability, the functionalized fabric can be subjected to typical laundering cycles in a washing machine. Due to its elasticity, the STEP-microfibers remain highly conductive and functional even after repeated washing. These superior properties highlight the high potential utility of the STEP-microfibers for wearable electronics into smart clothing applications. The STEP-microfiber can be embedded into a fabric glove and applied to various arterial sites to obtain physiological pulse waveforms. Other healthcare applications requiring pressure monitoring are also described.

Fabrication and Features of an Embodiment of the STEP-Microfiber.

To produce a STEP-microfiber, a soft, flexible, and stretchable microtube is made from silicone elastomer, polydimethylsiloxane (PDMS). This soft microtube serves as the insulating and deformable envelope of the STEP-microfiber. As described above with reference to FIGS. 1A-1E, eGaIn is injected into the tubular structure to form the conductive pathway. To enclose the microfibers, metal pins are inserted into the outlets and sealed with uncured elastomer. The metal pins can be easily connected to flexible PCB interconnects for electronics integration. In this manner, a highly conductive STEP-microfiber having a conductivity of 3.27±0.08 MS/m is produced, which is at least four orders of magnitude better than those previously reported.[16-18] Using this process, STEP-microfibers of various lumen diameters can be produced. This versatility enables the selection of different STEP-microfibers for various fabrics. The use of the liquid metallic alloy accounts for its high conductivity and deformability beyond the conventional limits attributed to mechanical fracture.

Figures 6A, 6B, 6C:
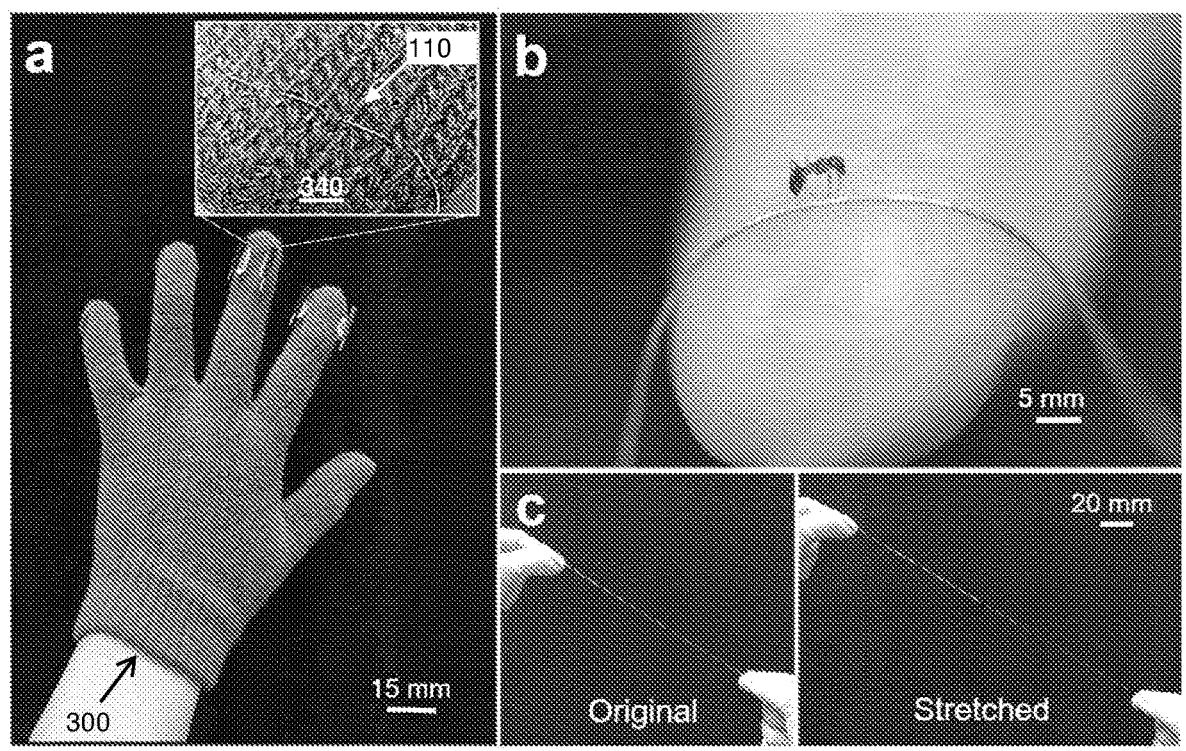
FIGS. 6A-6C illustrate a highly stretchable elastomeric piezo-resistive (STEP) microfiber that can be integrated in a fabric substrate.

FIG. 6A depicts a wearable device 300, here a glove, including a STEP-microfiber 110 woven in a fabric 340 substrate of the glove. The inset of FIG. 6A shows that the size of the microfiber 110 (Ø160 µm) is comparable to the cotton fabric yarns. FIG. 6A also illustrates a suitable position of the STEP-microfiber on the fabric glove, e.g., near the tip of a finger. The STEP-microfiber can only be clearly seen under a 4× optical magnification, highlighting its imperceptibility. Furthermore, the one-dimensional format of STEP-microfibers enables high compliance even to a highly curved three-dimensional surface of the cotton glove. In fact, the diameter of the STEP-microfiber is smaller than the size of an ant (FIG. 6B). The fabrication process, illustrated in FIGS. 1A-1D, and has also been reported.[19] Briefly, a customized dip coating technique was performed to create a uniform uncured elastomeric layer around a microscale metal wire. The wire was then removed to form the elastomeric microtubular structure. The STEP-microfiber shows high stretchability beyond 50% strain (FIG. 6C). Its high flexibility and stretchability allows the STEP-microfiber to be woven into a fabric using standard sewing and stitching processes.

Figures 13A, 13B, 13C:
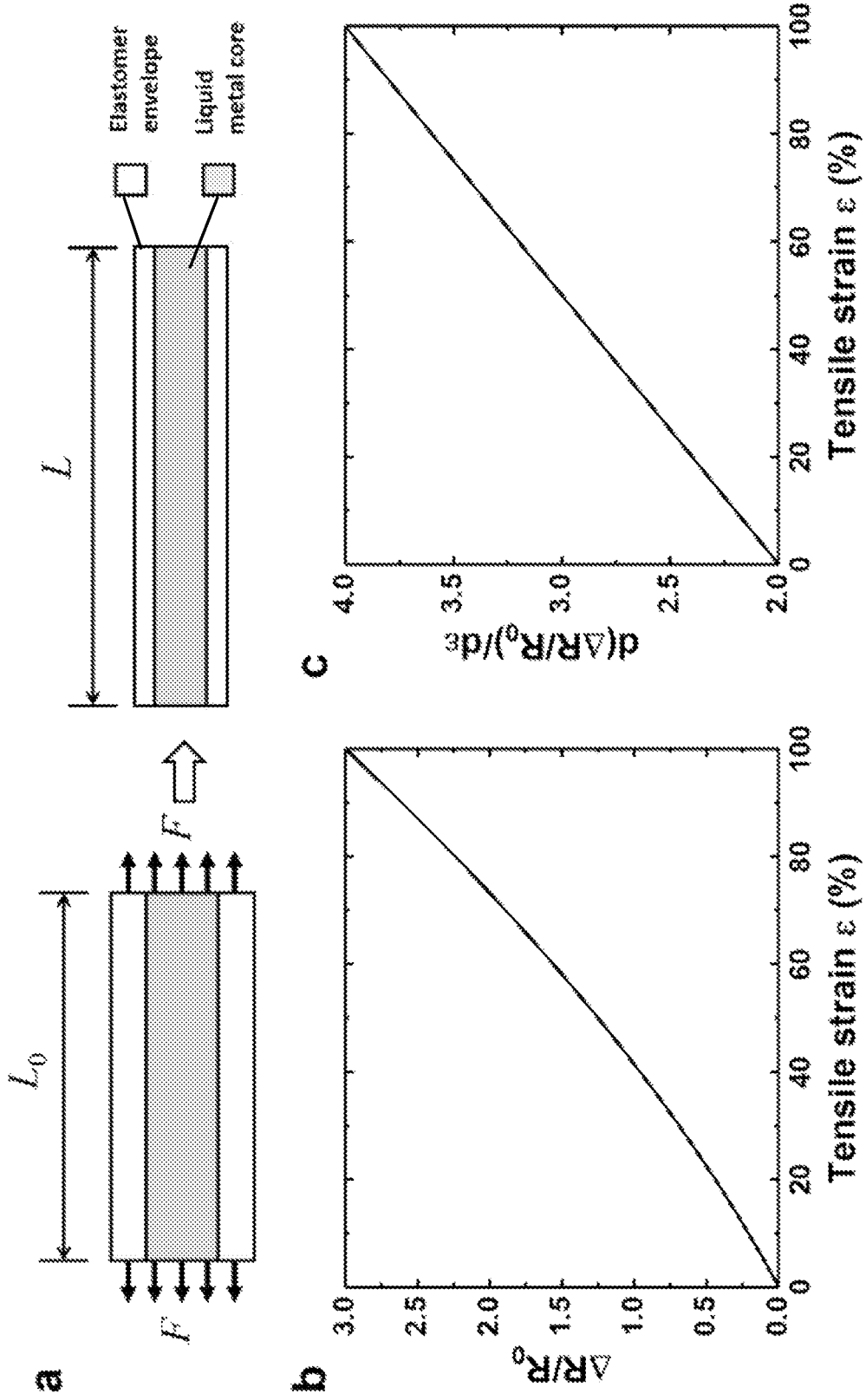
FIGS. 13A-13C illustrate a theoretical analysis of characteristics of a STEP-microfiber under tension.

The normalized resistance of the STEP-microfiber under tension can be calculated as $$\frac{\Delta R}{R_0} = \frac{R}{R_0} - 1 = \left(\frac{L}{L_0}\right)^2 - 1 \qquad (4)$$

where L represents the length of the microfiber, the subscript 0 denotes original value and ΔR is the change of resistance (see also FIGS. 13A-13C and Appendix: Theoretical Analysis). Notably, when the fiber is stretched, the resistance increases significantly due to the square law, implying a highly sensitive sensing element. On the other hand, when the STEP-microfiber is compressed, the fluid movement is different. The relationship between normalized resistance and normalized pressure can be expressed as $$\frac{\Delta R}{R_0} = \alpha \left[ \frac{1}{1 - (\lambda P)^2} - 1 \right] \quad (5)$$

where α represents the ratio between the length of the constricted portion and total length, λ is the correction factor based on the ratio of the outer diameter and the inner diameter of the microtubular envelope (see Appendix: Theoretical Analysis). For enhanced sensitivity, the ratio of the outer diameter and inner diameter has to be near to unity (FIGS. 14A-14C and Appendix: Theoretical Analysis).

Characteristics of Embodiments of the STEP-Microfiber Upon Different Loads.

Figures 7A, 7B, 7C, 7D:
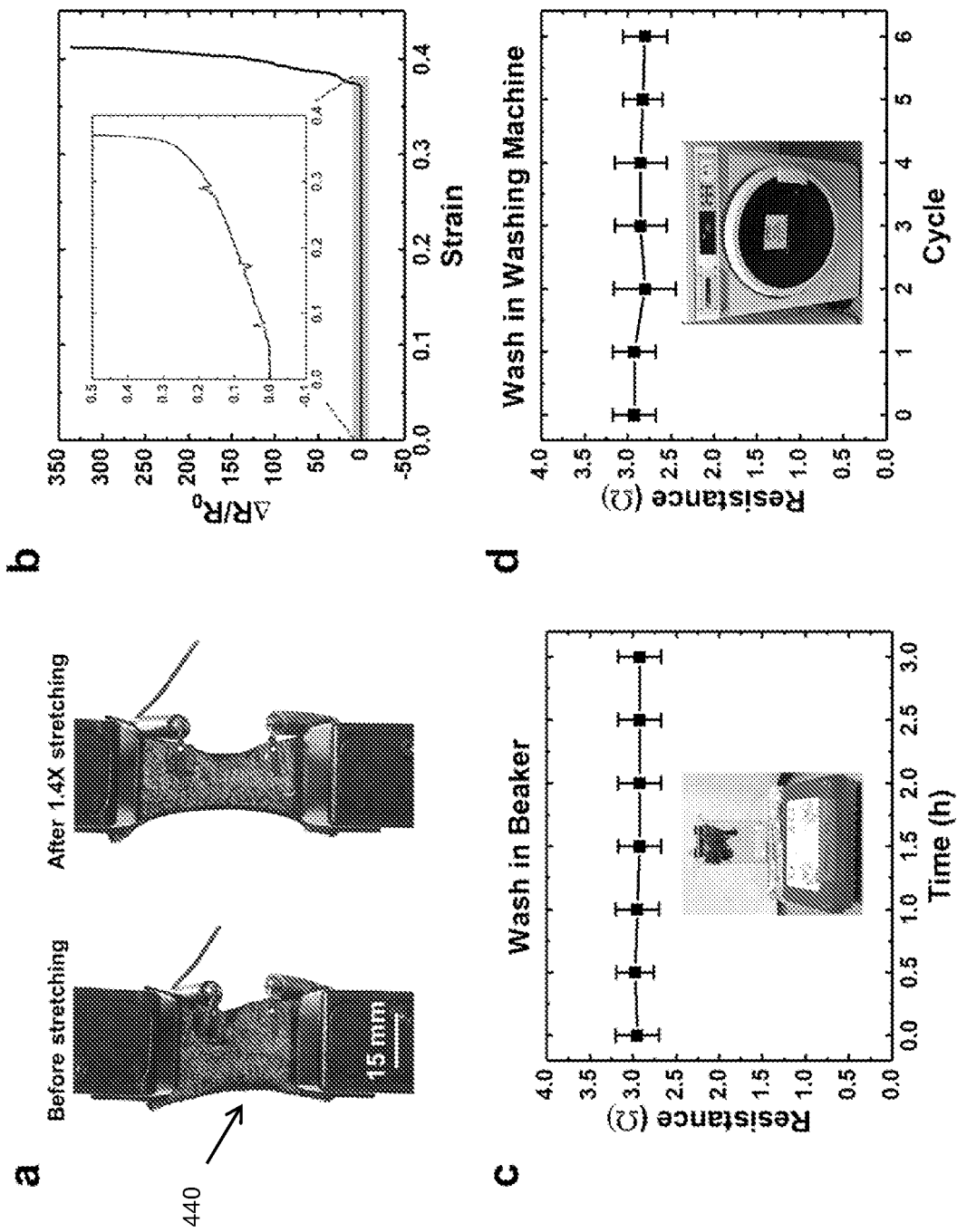
FIGS. 7A-7D illustrate characteristics of a STEP-microfiber upon different loads.

The PDMS-based STEP-microfiber enables high stretchability without damage. A tunable diameter of STEP-microfiber (between 100 μm and 1500 μm) may be achieved, realizing different stress-strain characteristics. This tunability allows the choice of different microfibers for various applications. To compare the durability of the STEP-microfiber to the textile, the STEP-microfiber is woven into the fabric and the smart textile 440 stretched using a universal loading machine (5848 MicroTester, Instron, Norwood, Mass.). FIG. 7A shows the experimental setup before and after stretching of smart textile 440. The normalized electrical resistance, defined by the resistance change over original resistance (ΔR/$R_0$), of the STEP-microfiber was recorded while the fabric was stretched (FIG. 7B). Here, it is observed that the normalized electrical resistance follows a linear increase up to 35% strain, suggesting a highly stretchable conductive microfiber. In fact, the small kinks in the normalized resistance represents textile yarns breaking at various strains (inset of FIG. 7B), yet the STEP-microfiber remains functional beyond these strains. This demonstrates the robustness of the STEP-microfiber under extreme deformations.

Moreover, a requirement for wearables is dependent on the functional elements to withstand laundering procedures. In fact, many conventional sensors suffer catastrophic failure due to the chemical reactions of the washing detergent coupled with heavy mechanical actions. However, in the STEP-microfiber, the conductive and sensing element eGaIn is confined within the silicone elastomeric microfiber, protecting it from external environment. Further, the conductive liquid maintains its liquid-state which allows shape reconfigurability even under extreme mechanical loadings and washing. Furthermore, eGaIn reacts spontaneously to form a thin surface oxide, which actually protects the inner core from chemical reaction (see FIG. 12, described below). To simulate washing, four STEP-microfibers were woven into a red dyed common woven fabric and subjected this textile to immersion and agitation in a beaker of 600 mL deionized water of temperatures above 32° C. (inset of FIG. 7C). The red dye was quickly cleansed from the fabric, showing high agitation and stirring within the beaker. The conductivity of the STEP-microfiber was measured before and after each experiment. Here, the conductivity of the STEP-microfiber remained unchanged despite continuous washing for 3 hours (FIG. 7C). To further demonstrate its washability, the textile was placed in a commercial washing machine together with 2 kg of ballast and liquid detergent, and subjected to washing steps according to the ISO 6330 standards). The laundering steps involved repeated washing, rinsing, and spinning cycles, lasting for 35 minutes. Notably, even after six cycles of wash, no change in functional integrity of the STEP-microfiber between each washing was observed (FIG. 7D). Furthermore, SEM images of the microfibers before washing (FIG. 11A) and after washing (FIG. 11B) showed no visible damage. Taken together, these results prove the high robustness and durability of STEP-microfibers even under repeated washing.

Pressure Sensing and Reliability Performance of Embodiments of the STEP-Microfiber.

Figure 8B:
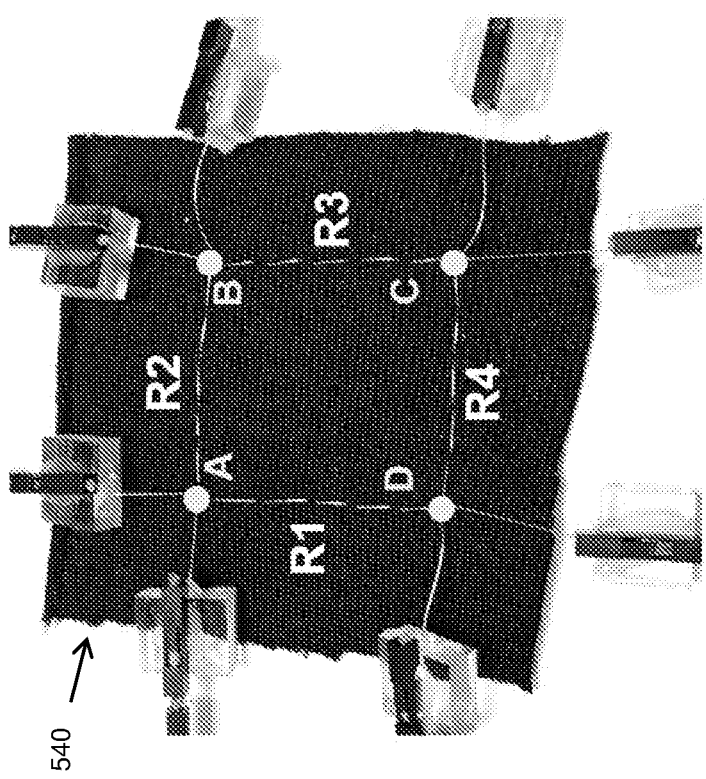
FIGS. 8A-8D illustrate pressure sensing and reliability performance of embodiments of the STEP-microfiber.
Figure 8A:
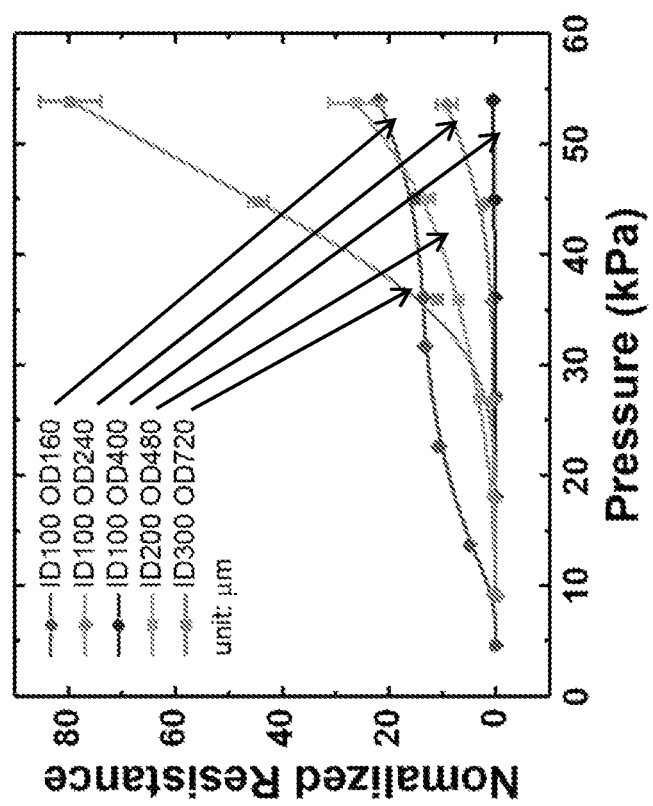
Figures 8C, 8D:
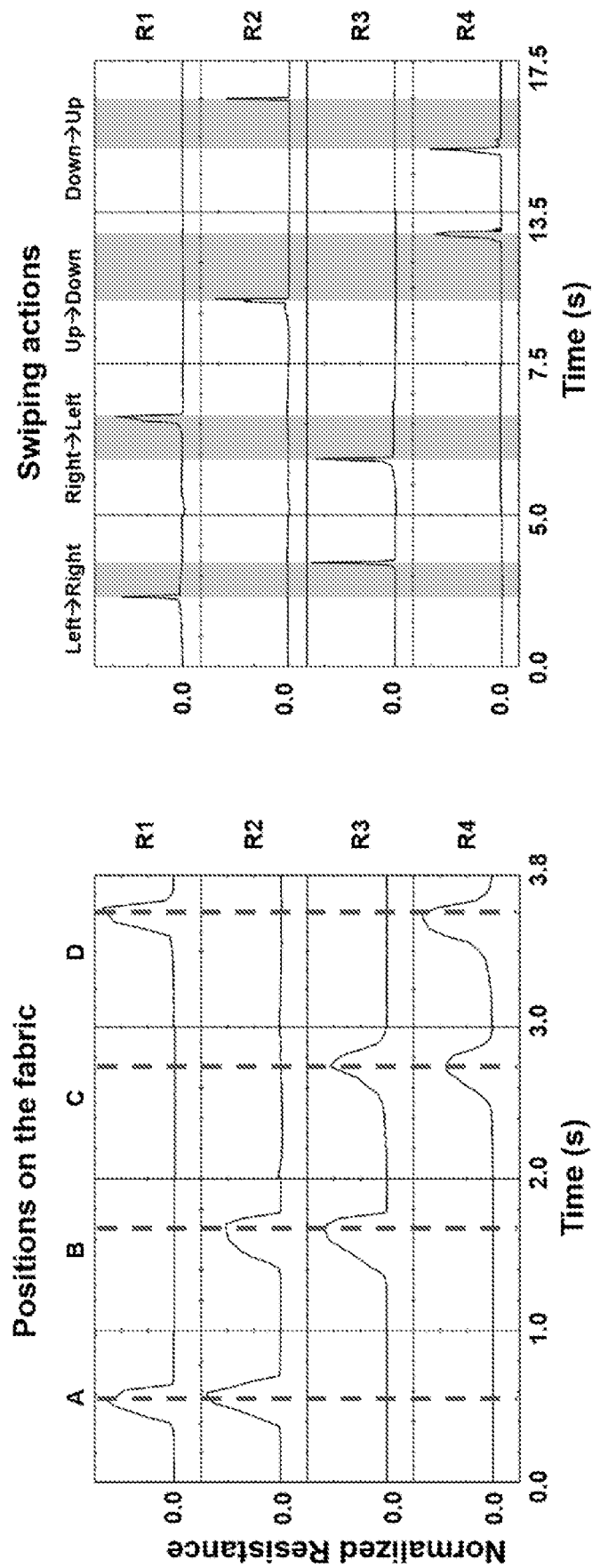
Figure 8E:
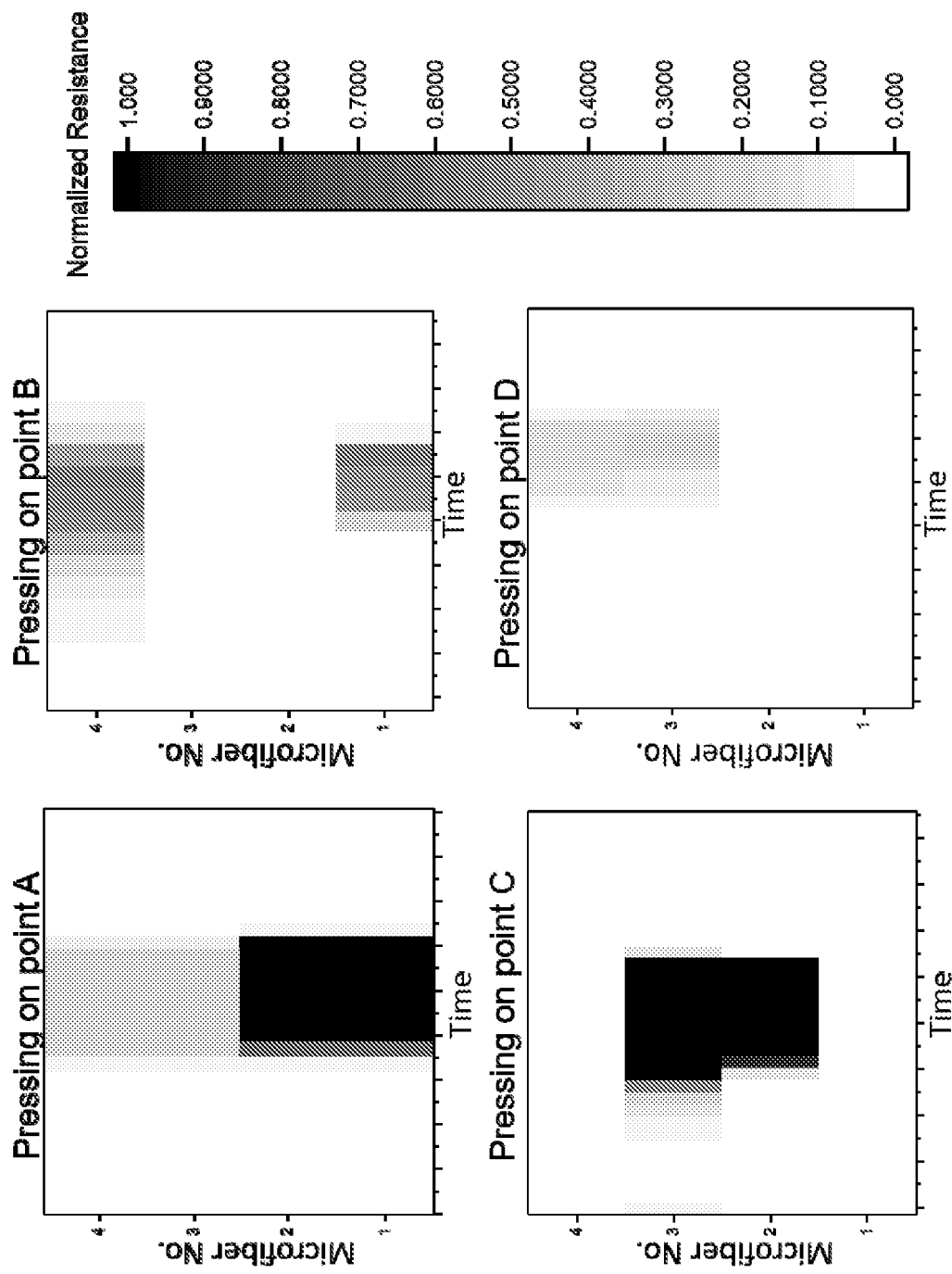
FIG. 8E illustrates a locational heat map of woven STEP-microfiber fabric. The heat map shows the peak electrical resistance intensity when different points (e.g., points A, B, C, D of FIG. 8B) were pressed on the STEP-microfibers woven into a fabric.
Figure 8F:
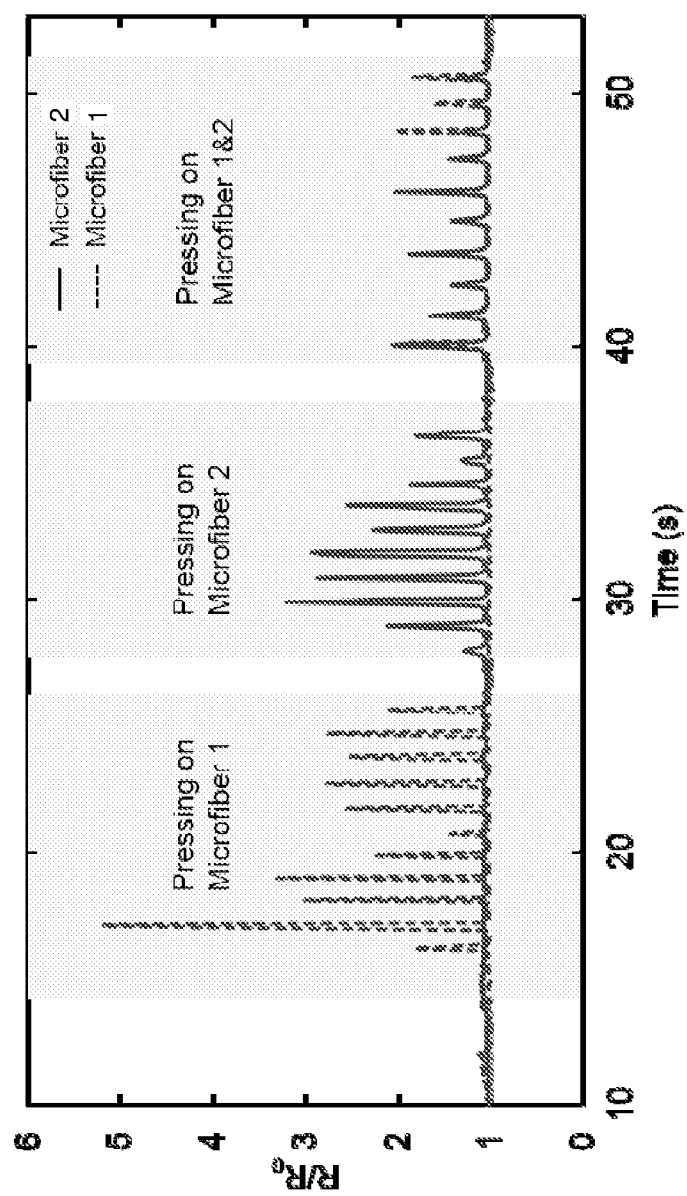
FIG. 8F illustrates multiple force sensing with woven STEP-microfiber fabric. The graph of relative electrical resistance shows the ability of the fabric to recognize different forces on individual microfibers, and simultaneous forces on both microfibers.
Figures 9A, 9B, 9C, 9D:
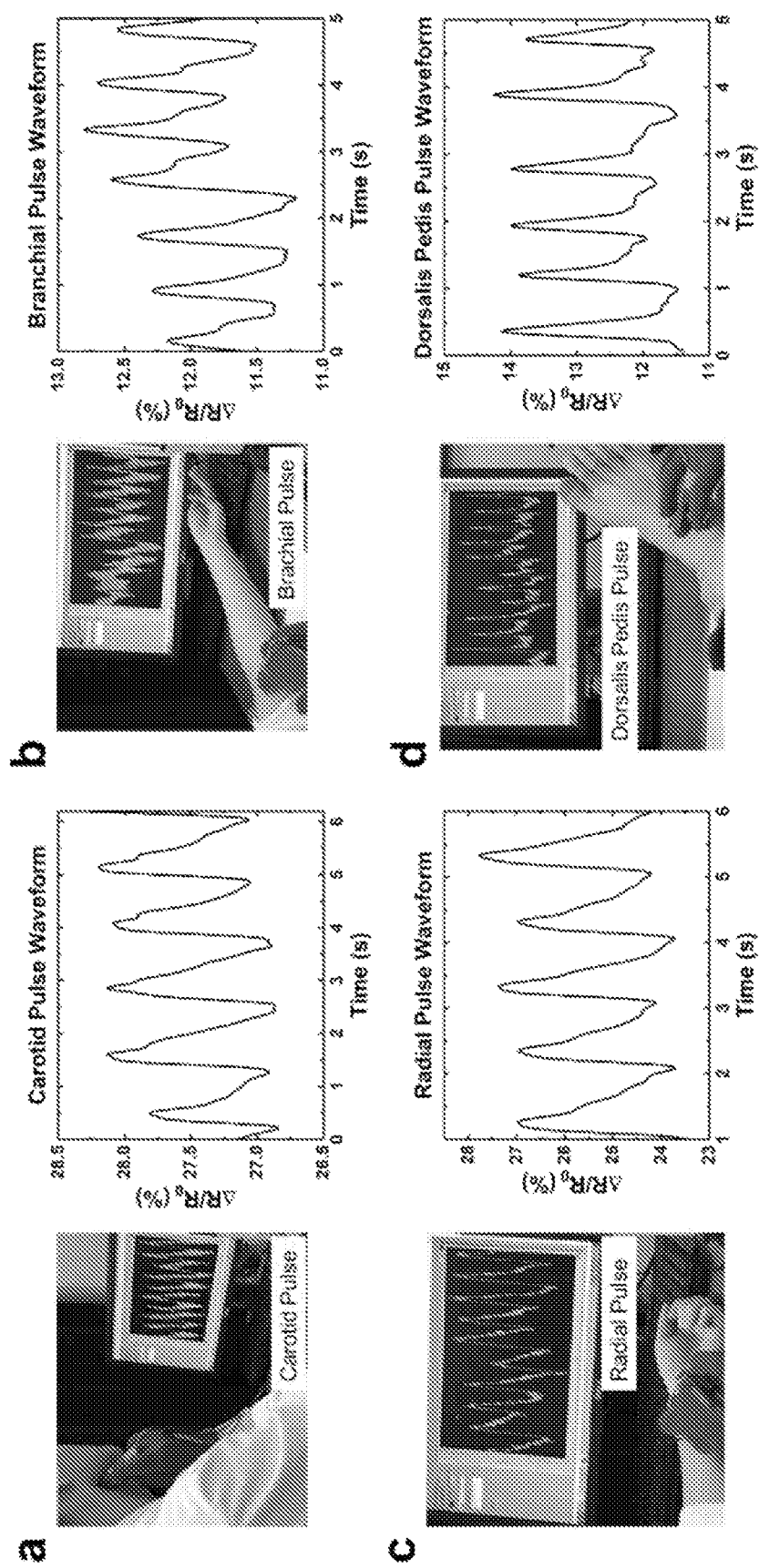
FIGS. 9A-9D illustrates pulse monitoring using a STEP-microfiber system embodiment.

Owing to the high conductivity of the liquid metallic alloy within the deformable elastomeric tubular envelope, the STEP-microfiber possesses force sensing capabilities as applied forces cause the liquid metallic alloy to be displaced within the microfiber. FIGS. 8A-8D illustrate the force sensing characteristics of embodiments of the STEP-microfiber with different diameters. The force sensitivity is dependent on the ratio of the inner diameter (ID) and the outer diameter (OD) of the tubular envelope (FIG. 8A). Again, this provides the choice of STEP-microfibers for different force sensing applications. Furthermore, due to the small size, STEP-microfibers (R1, R2, R3, R4) may be woven together in a fabric, forming a cross-stitched network 540 (3 cm×3 cm), as illustrated in FIG. 8B. Using a plurality of STEP-microfibers, both the magnitude and the location of the force applied may be determined by the spikes in the normalized electrical resistance)(ΔR/$R_o$) of corresponding STEP-microfibers. FIG. 8C illustrates the electrical signals when the corresponding positions on the fabric is pressed. Here, the signal peaks denote the force magnitude. By comparing the spatiotemporal electrical signals, the position of the force applied may be established. A localized heat map may also be produced based on the peak electrical intensities, enabling position and force recognition (FIG. 8E). Force directionality may also be computed by observing time lag of the signal peaks between STEP-microfibers (FIG. 8D). For example, when the user swipes from left to right, its corresponding time delay (vertical bands in FIG. 8D) of the electrical resistance between STEP-microfibers R1 and R3 denotes the force direction and its corresponding velocity. Multiple forces sensing is also possible with the STEP-microfibers woven fabric (FIG. 8F). The results strongly illustrate the potential of the STEP-microfibers for soft robotic and wearable human-computer interface applications.

Pulse Monitoring Using an Embodiment of the STEP-Microfiber System.

Real-time pulse monitoring has been of profound importance, especially for healthcare monitoring and disease diagnosis.[20, 21] To demonstrate the utility of the STEP-microfiber, the conductive microfiber is woven on a fully functional fabric, such as on a finger of the fabric glove (see, e.g., FIG. 6A). A user wearing the glove positioned the finger on various parts of the body, i.e., the wrist, the elbow pit, the neck, and the foot instep, to assess the arterial blood flow to the various parts of the body. As illustrated in FIGS. 9A-9D, arterial palpations can be obtained from radial, brachial, carotid, and dorsalis pedis arteries respectively, signifying its capability to perform real-time pulse recording and heart rate monitoring. Notably, similar pulse rates are measured across all the locations on the body, indicating its high sensitivity, responsiveness, and repeatability. Furthermore, by observing the subtle pulse differences based on the reference locations on the body, there is the potential to establish cardiac abnormalities,[22] such as arterial stiffness, atherosclerosis, or high blood pressure. Importantly, the subtle forces from the physiological flows captured by the STEP-microfiber can be recorded and displayed continuously in real-time, enabling versatility and robustness towards tele-rehabilitation applications and clinical diagnosis.

Other Example Applications of Embodiment of the STEP-Microfiber System.

Figures 10A, 10B, 10C, 10D, 10E:
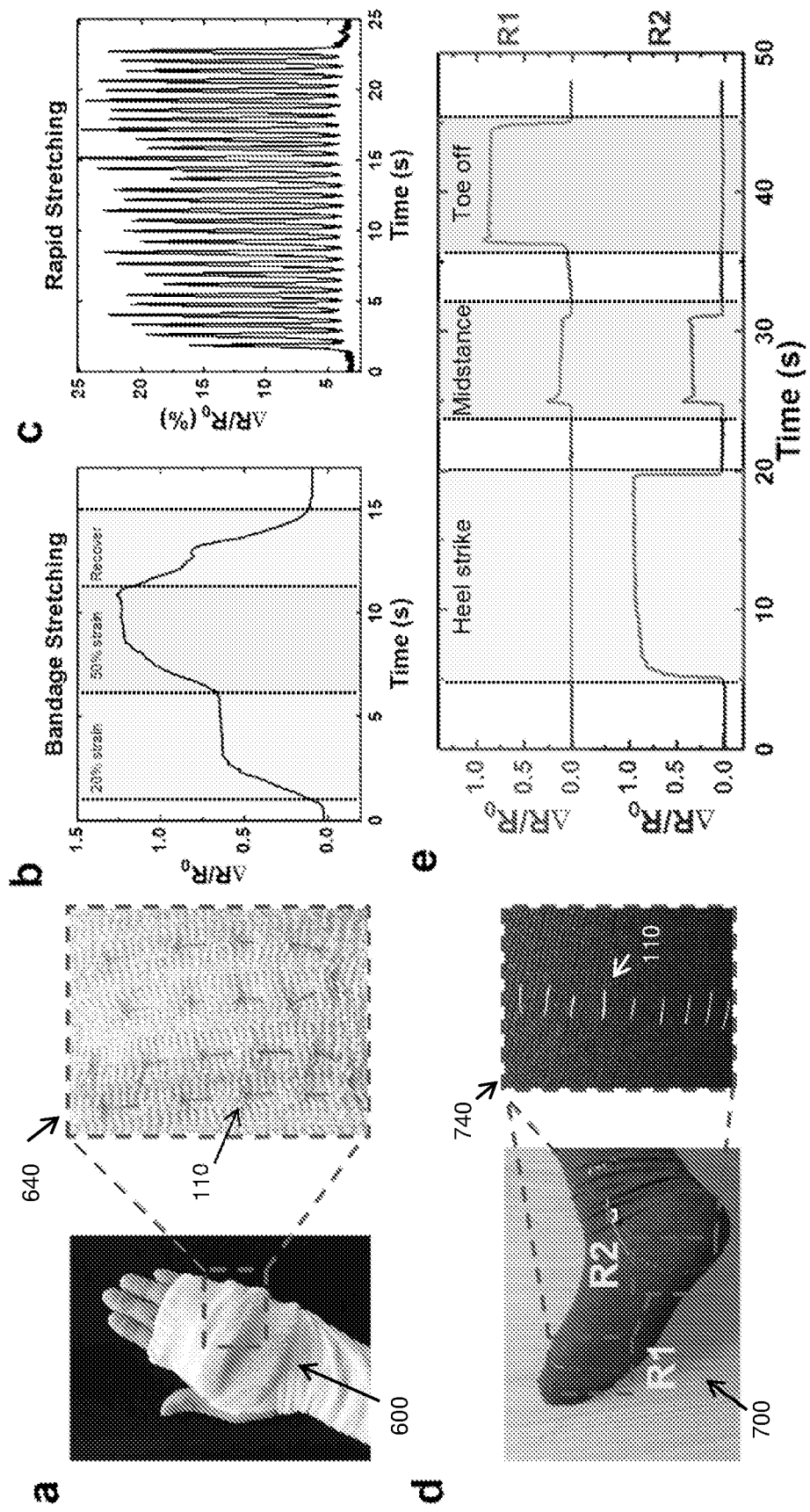
FIGS. 10A-10E show example applications of the STEP-microfiber system.

To further prove the versatility of the STEP-microfiber, the microfiber was woven into several fabric products. For example, the STEP-microfiber was sewn onto an elastic bandage 600 (PROFORE, Smith & Nephew, UK), as illustrated in FIG. 10A. In this embodiment, the conductive microfiber serves as a strain gauge on the bandage 600. The inset of FIG. 10A shows the micrograph of the STEP-microfiber 110 on the fabric 640 of the bandage 600. By measuring the electrical signal from the microfiber, the extent of the stretch on the bandage may be obtained (FIG. 10B). Different strain levels on the bandage may be achieved and quantified using the STEP-microfiber. Furthermore, the signals obtained were highly responsive (<100 ms) and repeatable, indicating low hysteresis and high durability (FIG. 10C). The deployment of the STEP-microfiber on the bandage is particularly useful for nurses and clinicians to ascertain the pressure applied over the dressings. Moreover, the STEP-microfiber can be woven into a sock 700, and this configuration can be used as means to measure plantar pressure (FIG. 10D). To demonstrate this, the STEP-microfibers were sewn onto the ball (R1) and heel (R2) of sock 700. The inset of FIG. 10D illustrates the microfibers 110 in the fabric 740 of the sock 700. A subject wearing the sock was asked to perform locomotion. As shown in FIG. 10E, when the heel strikes the ground, the electrical signal is immediately increased. Similarly, the gait cycle can be measured using the conductive microfiber sewn in the socks. Taken together, the STEP-microfiber provides high sensitivity and range for a wide variety of applications. Importantly, this enables the possibility of continuous remote monitoring for healthcare assessment and monitoring and paves the way for new kinds of electronic textiles.

The success of wearable electronics relies on a robust and versatile method of integrating conductive microfibers into fabrics. To this end, a multi-functional stretchable tubular elastomeric piezoresistive microfiber can be fabricated by incorporating liquid metallic alloy into soft microtubes. The resulting conductive microfiber is flexible, stretchable, robust, and durable. Even after repeated washing, the microfiber sustained no deterioration in electrical conductivity and functionality. In fact, weaving the conductive microfiber into existing fabrics, such as cotton glove, stretchable bandage, and socks, demonstrated viability of integrating the wearable STEP-microfiber into clothes or accessories. Furthermore, the conductive microfiber serves as a multifunctional sensor for force sensing, strain measurements, and even pulse recording. Integrating technologies with daily living is gradually becoming a norm and the notion of wearables is gaining in popularity. With the potential to be adopted and used on different fabrics, this inconspicuous sensor can pave the way as a novel and adaptable point-of-care testing for pressure sensing and pulse monitoring, with the potential to benefit patients and medical practitioners alike. The advance in sensing enables tremendous potential to extend tactile sensing unto future wearable electronics, such as robotics, prosthetics, healthcare monitoring devices, and artificial skins, with exceptional ease and effectiveness.

Example 5—Device Design and Fabrication

To produce the STEP-microfiber, a metal filament was first immersed vertically into a freshly mixed PDMS base and curing agent (w/w 10:1). The metal filament was drawn out of the uncured elastomer pool and cured by rapid heating at ~150° C. Next, the metal wire was peeled off during a sonication process in acetone bath. The detached elastomeric microtube was then baked in an oven for 2 hours to remove any acetone remnant. Subsequently, liquid metallic alloy eGaIn was injected into the microtube using a 1 mL syringe. Metal wires were then inserted into the outlets and sealed using uncured silicone elastomer. The entire device is brought into the oven at 75° C. for another 30 minutes to obtain the final product. To sew the STEP-microfiber onto the fabric, the microfiber is passed through the eye of the sewing needle and woven into the existing fabric.

Example 6—Pressure Sensing, Durability, and Mechanical Forces Differentiation

The STEP-microfiber was subjected to compressive ramp-hold-release loads starting from 0.5 to 6 N using a universal load machine (5848 MicroTester, Instron, Norwood, Mass.). The ramp and release rates were set at 5 mm/min. The electrical response was continuously monitored and recorded using PXIe 4081 Digital Multimeter (National Instruments, Austin, Tex.).

Example 7—Washing/Laundering Procedures

When performing washing in the beaker, the textile with woven STEP microfibers was briefly immersed in red dye before placing it in the beaker of 600 mL deionized water (see, e.g., FIG. 7C). A magnetic stirring bar was inserted into the beaker of water and then the stirring rate was set to 180 revolutions per minute (rpm). To immerse the electronic textile into water, it was clamped by two binder clips and hung on a plastic bar spanning on the beaker. Another two binder clips clamping on the bottom of the fabric served as weight to achieve good immersion. Next, the stirring rate was increased to 1110 rpm. Every 30 minutes the textile was lifted out to measure the resistance of the four STEP-microfibers sewn in it. The water temperature was measured to be above 32° C. throughout the test.

When performing washing in the washing machine, the same textile was placed together with 2 kg ballast into a Maytag MHN30PN 9 kg Commercial Front Load Washing Machine (see, e.g., FIG. 7D). According to vendor guidance, ½ cap of Breeze Power Clean Liquid Detergent was added into the washing machine before laundering. The laundering steps involved repeated washing, rinsing, and spinning cycles, lasting for 35 minutes. After each washing, the STEP-Fabric was taken out to record the electrical resistances of the STEP-microfibers using a RS-12 Compact Digital Multimeter.

Example 8—Glove Sensing

To validate the capability of the STEP-microfiber to measure pulse pressure, the microfiber was woven on the fingertips of a fabric glove (see, e.g., FIG. 6A). Written informed consent was obtained from all participants prior to the experiments. The subject was requested to sit still for a few seconds and the pulse was measured by placing the fingertips on the subject's wrist, elbow pit, neck, and foot instep (see, e.g., FIGS. 9A-9D). Electrical signals were recorded and displayed continuously in real time using PXIe 4081 Digital Multimeter (National Instruments, Austin, Tex.). The electrical signals were further processed using a MATLAB filter and pulse rate was calculated by counting the period of each waveform.

Example 9—STEP-Microfiber Hybrid Solid-Liquid Composite

Eutectic Gallium Indium (75.5% Gallium, 24.5% Indium by weight) and all other chemicals were obtained from Sigma-Aldrich. Its low viscosity enables high moldability and can be jetted into the tubular structures by needle injection. Owing to its high surface tension, the entire tubular structure can be completed filled without interruptions. Polydimethylsiloxane, SYLGARD 184 was obtained from Dow Corning Inc., and cured by mixing precursor and curing agent in 10:1 w/w ratio. The air permeable silicone elastomer layer enables the gallium-based alloy to react spontaneously to form a thin, native skin of gallium oxide, which is a wide band-gap semiconductor (~4.8 eV at room temperature). FIG. 12 is a schematic illustration of the STEP-microfiber composite. Both the silicone elastomer and the gallium oxide skin layer work together to protect the conductive eutectic Gallium Indium against mechanical and chemical perturbations.

APPENDIX—THEORETICAL ANALYSIS

Theoretical Analysis of STEP-Microfiber Under Tension
The resistance of the STEP-microfiber is $$R = \frac{\rho L}{A} = \frac{\rho L^2}{V} \tag{A1}$$

where $\rho$ is the resistivity of the liquid metal eGaIn, L is the length of the microfiber, A is the cross-sectional area of the lumen of the microfiber and V is the volume of the eGaIn enclosed in the microfiber.

Due to the incompressibility of liquid, the volume of the enclosed eGaIn is constant, $$V = AL = \text{constant} \tag{A2}$$

Therefore, the normalized resistance is given by equation (4) above, reproduced here as $$\frac{\Delta R}{R_0} = \frac{R}{R_0} - 1 = \left(\frac{L}{L_0}\right)^2 - 1 \tag{A3}$$

where subscript 0 denotes original value and $\Delta R$ is the change of resistance.

On the other hand, the tensile strain of the STEP-microfiber is $$\varepsilon = \frac{\Delta L}{L_0} = \frac{L}{L_0} - 1 \tag{A4}$$

Substitute equation (A4) into (A3) and the relation between normalized resistance and tensile strain is $$\frac{\Delta R}{R_0} = (1 + \varepsilon)^2 - 1 \tag{A5}$$

The sensitivity of the STEP-microfiber is calculated as the derivative of normalized resistance, $$\frac{d}{d\varepsilon}\left(\frac{\Delta R}{R}\right) = 2(1 + \varepsilon) \tag{A6}$$

Therefore, the sensitivity increases linearly with increasing tensile strain.

Theoretical Analysis of STEP-Microfiber Under Compression

Assume near the middle of the STEP-microfiber, a small portion of it is subject to compression. The length of this portion is $L_c$ and the total length of the microfiber is L. Let $\alpha = L_c/L$ and we consider the constricted portion is small when $\alpha < 0.1$. Let $R_c$ be the resistance of the portion under compression. For the whole microfiber, its normalized resistance is $$\frac{\Delta R}{R_0} = \frac{R_c - R_{c0}}{R_0} = \frac{R_{c0}}{R_0}\left(\frac{R_c}{R_{c0}} - 1\right) \tag{A7}$$

where $\Delta R$ is the change of resistance, subscript 0 denotes original value and subscript c denotes the portion under compression.

Figures 14A, 14B, 14C:
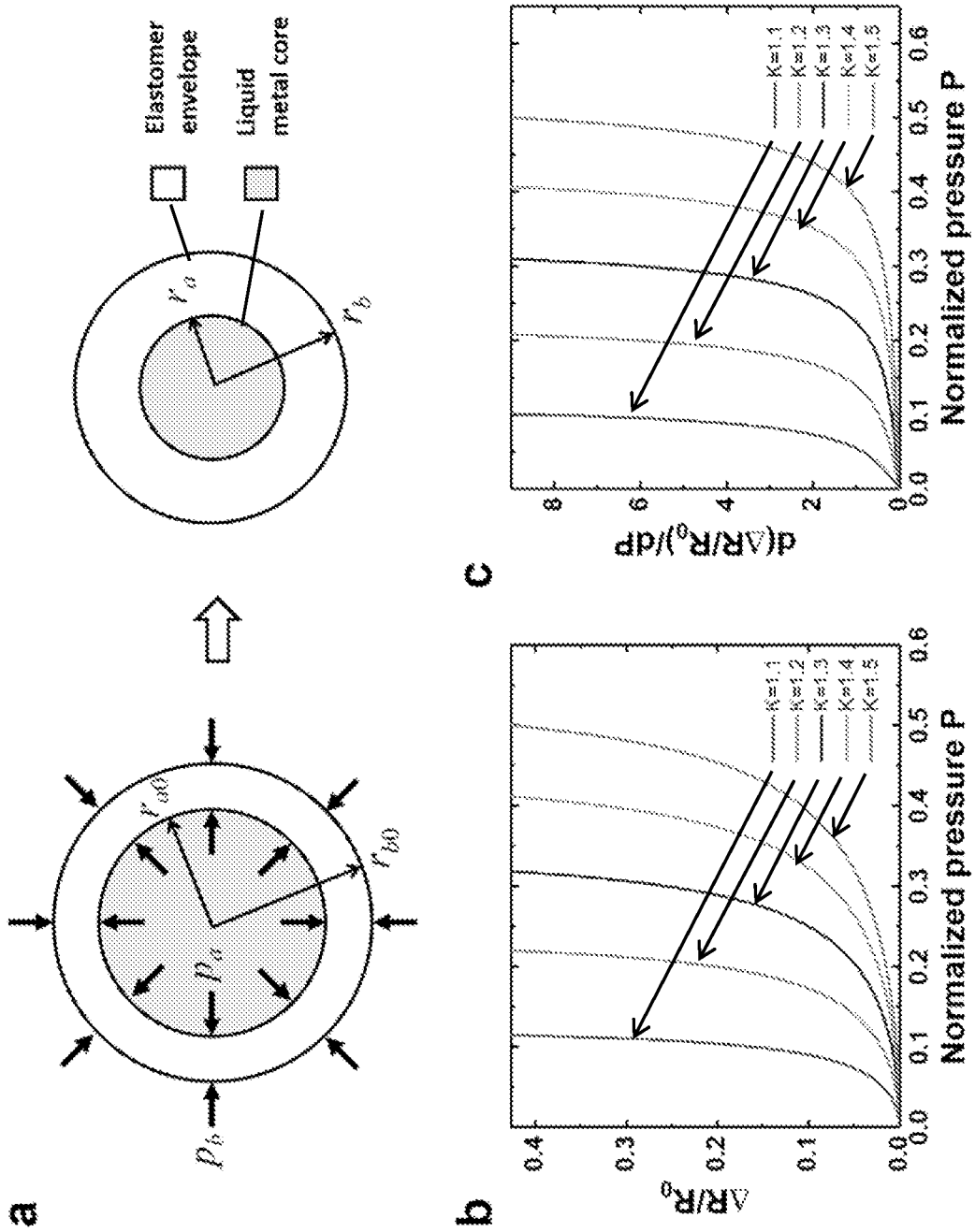
FIGS. 14A-14C illustrate a theoretical analysis of the characteristics of a STEP-microfiber under compression.

From the theory of elasticity, the deformation of a tubular structure shown in FIG. 14A is $$u_r = \frac{1+v}{E}\left[-\frac{r_{a0}^2 r_{b0}^2 (p_b - b_a)}{r_{b0}^2 - r_{a0}^2}\frac{1}{r} + (1 - 2v)\frac{r_{a0}^2 p_a - r_{b0}^2 p_b}{r_{b0}^2 - r_{a0}^2}\right] \tag{A8}$$

where $u_r$ is the radial displacement, E is the Young's modulus, v is the Poisson's ratio, r is the radial coordinate ($r_{a0} \leq r \leq r_{b0}$), $r_{a0}$ is the inner radius, $r_{b0}$ is the outer radius, $p_a$ is the pressure applied on the inner surface, $p_b$ is the pressure applied on the outer surface and 0 in the subscripts denotes original value.

As the STEP-microfiber is sewn into fabrics, we assume the pressure applied on the fabric p is evenly distributed around the microfiber. In addition, the liquid metal in the constricted portion readily redistributes to non-constricted portion. Given that the constricted portion is small compared to the total length, we assume the liquid metal does not cause pressure on the inner surface of the microfiber and the length of the microfiber L does not change. Based on these assumptions, we have $p_a = 0$ and $p_b = p$.

Due to the outer pressure p, the inner diameter decreases from $d_{a0}$ to $d_a$ and the outer diameter decreases from $d_{b0}$ to $d_b$. Let $D_{aa} = d_a/d_{a0}$ and $D_{bb} = d_b/d_{b0}$, we have $$D_{aa} = \frac{d_a}{d_{a0}} = \frac{r_{a0} + u_r(r_{a0})}{r_{a0}} \tag{A9}$$

and $$D_{bb} = \frac{d_b}{d_{b0}} = \frac{r_{b0} + u_r(r_{b0})}{r_{b0}} \tag{A10}$$

Let $r=r_{a0}$ in equation (A8), then substitute into (A9)

$$D_{aa} = 1 + \frac{2(1+v^2)}{E} \frac{r_{b0}^2}{r_{a0}^2 - r_{b0}^2} p \tag{A11}$$

Also, let $r=r_{b0}$ in equation (A8), then substitute into (A10), $$D_{bb} = 1 + \frac{1+v}{E} \frac{r_{a0}^2 + (1-2v)r_{b0}^2}{r_{a0}^2 - r_{b0}^2} p \tag{A12}$$

Let $$K = \frac{r_{b0}}{r_{a0}} = \frac{d_{b0}}{d_{a0}}$$

be the ratio of outer diameter to inner diameter at original state, and normalized pressure $$P = \frac{p}{E}.$$

Note $K>1$ and $P>0$. Equations (A11) and (A12) become $$D_{aa} = 1 + 2(1-v^2)\frac{K^2}{1-K^2} P \tag{A13}$$

$$D_{bb} = 1 + (1+v)\frac{1+(1-2v)K^2}{1-K^2} P \tag{A14}$$

The cross-sectional area $A_0$ decreases to A, $$\frac{A_0}{A} = \frac{d_{b0}^2 - d_{a0}^2}{d_b^2 - d_a^2} \tag{A15}$$

$$= \frac{1}{(d_b/d_{b0})^2 - (d_a/d_{b0})^2} - \frac{1}{(d_b/d_{a0})^2 - (d_a/d_{a0})^2}$$

Let $D_{ab}=d_a/d_{b0}$ and $D_{ba}=d_b/d_{a0}$, then $$\frac{A_0}{A} = \frac{1}{D_{bb}^2 - D_{ab}^2} - \frac{1}{D_{ba}^2 - D_{aa}^2} \tag{A16}$$

Note that $$D_{ab} = \frac{d_a}{d_{b0}} = \frac{d_a}{d_{a0}} \frac{d_{a0}}{d_{b0}} = \frac{D_{aa}}{K} \tag{A17}$$

$$D_{ba} = \frac{d_b}{d_{a0}} = \frac{d_b}{d_{b0}} \frac{d_{b0}}{d_{a0}} = KD_{bb} \tag{A18}$$

Therefore, $$\frac{A_0}{A} = \frac{K^2 - 1}{K^2 D_{bb}^2 - D_{aa}^2} \tag{A19}$$

The resistance of the constricted portion increases from $R_{c0}$ to $R_c$, $$\frac{R_c}{R_{c0}} = \frac{\rho L_c / A}{\rho L_c / A_0} = \frac{A_0}{A} \tag{A20}$$

Here, $\rho$ is the resistivity of the liquid metal core.
Substitute equations (A13), (A14) into (A19) and note $v \approx 0.5$ for the elastomer envelope. From (A20), we obtain $$\frac{R_c}{R_{c0}} = \frac{1}{1 - (\lambda P)^2} \tag{A21}$$

where $$\lambda = \frac{3}{2} \frac{K}{K^2 - 1} > 0 \tag{A22}$$

Note that $R_{c0}/R_0 = L_c/L = \alpha$, and substitute equation (A21) into (A7), we obtain the relation between normalized resistance and normalized pressure as equation (5), reproduced here as $$\frac{\Delta R}{R_0} = \alpha \left[ \frac{1}{1 - (\lambda P)^2} - 1 \right] \tag{A23}$$

The sensitivity of the sensor is calculated as the derivative of normalized resistance, $$\frac{d}{dP}\left(\frac{\Delta R}{R_0}\right) = \frac{2\alpha \lambda^2 P}{[1 - (\lambda P)^2]^2} \tag{A24}$$

As an example, let $\alpha=0.1$, FIGS. 14B-14C shows different responses of the STEP-microfiber when K=1.1, 1.2, 1.3, 1.4 and 1.5, from which we know both the normalized resistance $\Delta R/R_0$ and the sensitivity of the STEP-microfiber sewn in fabrics nonlinearly increase with increasing normalized pressure P. In addition, when K is smaller, e.g., smaller outer diameter and same inner diameter, the STEP-microfiber is more sensitive, but the detection range in terms of normalized pressure is narrower.

Equations (A23) and (A24) are valid only when P is less than a certain value. Note that $d_a>0$ and $d_b-d_a>0$ should always hold during compression, i.e., $D_{aa}>0$ and $KD_{bb}-D_{aa}>0$. Note that $v \approx 0.5$ and equations (A13), (A14), we have $$D_{aa} = 1 - K\lambda P > 0 \tag{A25}$$

$$KD_{bb} - D_{aa} = (K-1)(1+\lambda P) > 0 \tag{A26}$$

From equation (A25) we know, $$P < \frac{1}{K\lambda} < \frac{1}{\lambda} \tag{A27}$$

In addition, because K>1, λ>0 and P>0, equation (A26) always holds.

REFERENCES

[1] I. K. Silverman, W. T. Moody, Journal of the Franklin Institute 1965, 279, 374.
[2] I. D. Johnston, D. K. McCluskey, C. K. L. Tan, M. C. Tracey, Journal of Micromechanics and Microengineering 2014, 24, 035017.
[3] D. Quéré, Annual Review of Fluid Mechanics 1999, 31, 347.
[4] S. Grilli, S. Coppola, V. Vespini, F. Merola, A. Finizio, P. Ferraro, Proceedings of the National Academy of Sciences 2011, 108, 15106.
[5] R. Li, B. Nie, P. Digiglio, T. Pan, Microflotronics: A Flexible, Transparent, Pressure-Sensitive Microfluidic Film. Advanced Functional Materials 2014, 24, 6195-6203.
[6] F. Cai, C. Yi, S. Liu, Y. Wang, L. Liu, X. Liu, X. Xu, L. Wang, Biosensors and Bioelectronics 2016, 77, 907.
[7] S. Gong, W. Schwalb, Y. Wang, Y. Chen, Y. Tang, J. Si, B. Shirinzadeh, W. Cheng, Nature Communications 2014, 5, 3132.
[8] W. W. Nichols, American Journal of Hypertension 2005, 18, 3S.
[9] A. P. Avolio, L. M. Van Bortel, P. Boutouyrie, J. R. Cockcroft, C. M. McEniery, A. D. Protogerou, M. J. Roman, M. E. Safar, P. Segers, H. Smulyan, Hypertension 2009, 54, 375.
[10] D. Shinji, H. Junya, Y. Sho, S. M. Tsubasa, Journal of Micromechanics and Microengineering 2015, 25, 097002.
[11] Zhu, S.; So, J.-H.; Mays, R.; Desai, S.; Barnes, W. R.; Pourdeyhimi, B.; Dickey, M. D., Ultrastretchable Fibers with Metallic Conductivity Using a Liquid Metal Alloy Core. Advanced Functional Materials 2013, 23 (18), 2308-2314.
[12] Harada, S.; Kanao, K.; Yamamoto, Y.; Arie, T.; Akita, S.; Takei, K., Fully Printed Flexible Fingerprint-like Three-Axis Tactile and Slip Force and Temperature Sensors for Artificial Skin. ACS Nano 2014, 8 (12), 12851-12857.
[13] Liu, T.; Inoue, Y.; Shibata, K., A Small and Low-Cost 3-D Tactile Sensor for a Wearable Force Plate. IEEE Sensors Journal 2009, 9 (9), 1103-1110.
[14] Lee, H. K.; Chung, J.; Chang, S. I.; Yoon, E., Normal and Shear Force Measurement Using a Flexible Polymer Tactile Sensor With Embedded Multiple Capacitors. Journal of Microelectromechanical Systems 2008, 17 (4), 934-942.
[15] Park, Y.-L.; Majidi, C.; Kramer, R.; Bérard, P.; Wood, R. J., Hyperelastic pressure sensing with a liquid-embedded elastomer. Journal of Micromechanics and Microengineering 2010, 20 (12), 125029.
[16] Li, Y.; Zhu, H.; Shen, F.; Wan, J.; Han, X.; Dai, J.; Dai, H.; Hu, L. Highly Conductive Microfiber of Graphene Oxide Templated Carbonization of Nanofibrillated Cellulose. Adv. Funct. Mater. 2014, 24 (46), 7366-7372.
[17] Li, Y.; Zhu, H.; Wang, Y.; Ray, U.; Zhu, S.; Dai, J.; Chen, C.; Fu, K.; Jang, S.-H.; Henderson, D.; Li, T.; Hu, L. Cellulose-Nanofiber-Enabled 3D Printing of a Carbon-Nanotube Microfiber Network. Small Methods 2017, 1 (10), 1700222.
[18] Yun, Y. J.; Ah, C. S.; Hong, W. G.; Kim, H. J.; Shin, J.-H.; Jun, Y. Highly Conductive and Environmentally Stable Gold/graphene Yarns for Flexible and Wearable Electronics. Nanoscale 2017, 9 (32), 11439-11445.
[19] Xi, W.; Kong, F.; Yeo, J. C.; Yu, L.; Sonam, S.; Dao, M.; Gong, X.; Lim, C. T. Soft Tubular Microfluidics for 2D and 3D Applications. Proc. Natl. Acad. Sci. 2017, 114 (40), 10590-10595.
[20] Yang, T.; Jiang, X.; Zhong, Y.; Zhao, X.; Lin, S.; Li, J.; Li, X.; Xu, J.; Li, Z.; Zhu, H. A Wearable and Highly Sensitive Graphene Strain Sensor for Precise Home-Based Pulse Wave Monitoring. ACS Sensors 2017, 2 (7), 967-974.
[21] Chen, L. Y.; Tee, B. C. K.; Chortos, A. L.; Schwartz, G.; Tse, V.; J. Lipomi, D.; Wong, H. S. P.; McConnell, M. V.; Bao, Z. Continuous Wireless Pressure Monitoring and Mapping with Ultra-Small Passive Sensors for Health Monitoring and Critical Care. Nat. Commun. 2014, 5.
[22] Park, D. Y.; Joe, D. J.; Kim, D. H.; Park, H.; Han, J. H.; Jeong, C. K.; Park, H.; Park, J. G.; Joung, B.; Lee, K. J. Self-Powered Real-Time Arterial Pulse Monitoring Using Ultrathin Epidermal Piezoelectric Sensors. Adv. Mater. 2017, 29 (37).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A microtube sensor, comprising:
   a flexible microtube comprising a polymer and defining a lumen, the flexible microtube having (i) an inner diameter of about 10 μm to about 200 μm and an outer diameter, and (ii) a wall having a uniform thickness surrounding the lumen, the wall having a uniform thickness of about 10 μm to about 40 μm; and
   a liquid-state conductive element within the lumen of the flexible microtube, the flexible microtube having closed ends to retain the liquid-state conductive element in the lumen,
   wherein the microtube sensor has a property that a change in electrical resistance of the liquid-state conductive element is indicative of a force-induced deformation of the flexible microtube,
   wherein the force sensitivity of the sensor is about 2.8 $N^{-1}$ to about 68 $N^{-1}$ for static force loads from about 5 mN to about 900 mN.

2. The microtube sensor of claim 1, wherein the polymer is a silicone elastomer, an ultraviolet sensitive polymer, polyurethane, a conductive polymer, conductive rubber, polyimide, a thermoset polymer or a thermoplastic polymer.

3. The microtube sensor of claim 2, wherein the silicone elastomer is polydimethylsiloxane, phenyl-vinyl silicone, methyl-siloxane, fluoro-siloxane or platinum cured silicone rubber.

4. The microtube sensor of claim 2, wherein the ultraviolet sensitive polymer is a fluorinated resin with acrylate/methacrylate groups, styrene-acrylate-containing polymer, polyacrylate polyalkoxy silane, a positive photoresist, a negative photoresist, diazonaphthoquinone-based positive photoresist or epoxy-based negative photoresist.

5. The microtube sensor of claim 1, wherein the liquid-state conductive element is a liquid metallic alloy.

6. The microtube sensor of claim 5, wherein the liquid metallic alloy is eutectic gallium-indium-tin or eutectic gallium-indium (eGaIn).

7. The microtube sensor of claim 1, wherein a ratio of the outer diameter to the inner diameter is about 1.05 to about 1.11.

8. The microtube sensor of claim 1, wherein the length of the microtube is about 1 m or less.

9. The microtube sensor of claim 1, wherein the microtube has a circular, elliptical, rectangular, square, triangular, star, non-circular, or irregular cross-sectional shape.

10. The microtube sensor of claim 1, further comprising connectors at the ends of the microtube and in electrical contact with the liquid-state conductive element, to measure the electrical resistance of the liquid-state conductive element.

11. A method of sensing force, comprising:
exposing the microtube sensor of claim 1 to a mechanical force; and
measuring the change in the electrical resistance of the liquid-state conductive element within the lumen of the flexible microtube in response to the mechanical force, wherein the change in the electrical resistance of the liquid-state conductive element is indicative of the force-induced deformation of the flexible microtube.

12. The method of claim 11, further comprising using the measured change in the electrical resistance to monitor a physiological parameter.

13. The method of claim 12, wherein the physiological parameter is at least one of pulse pressure, blood pressure, heart rate, foot pressure, tactile force and tremor.

14. The microtube sensor of claim 1, wherein the microtube sensor is woven into a fabric substrate.

15. A wearable electronic device, comprising:
a fabric substrate configured to be worn on a body; and
a microfiber woven into the fabric substrate, the microfiber comprising the microtube sensor of claim 1.

16. The microtube sensor of claim 1, wherein the outer diameter is less than 120 μm.

17. The microtube sensor of claim 1, wherein the outer diameter is from about 100 μm to about 200 μm.

18. The microtube sensor of claim 1, wherein the sensor can measure strain, pressure or a combination of these.

19. A method of making a microtube sensor, comprising:
providing a flexible microtube comprising a polymer and defining a lumen, the flexible microtube having (i) an inner diameter of about 10 μm to about 200 μm and an outer diameter, and (ii) a wall having a uniform thickness surrounding the lumen, the wall having a uniform thickness of about 10 μm to about 40 μm;
injecting a liquid-state conductive element into the lumen of the flexible microtube; and
closing ends of the flexible microtube to retain the liquid-state conductive element in the lumen, to thereby make the microtube sensor that has a property that a change in electrical resistance of the liquid-state conductive element is indicative of a force-induced deformation of the flexible microtube,
wherein the force sensitivity of the sensor is about $2.8\ N^{-1}$ to about $68\ N^{-1}$ for static force loads from about 5 mN to about 900 mN.

20. The method of claim 19, further comprising:
placing connectors at the ends of the microtube and in electrical contact with the liquid-state conductive element, to measure the electrical resistance of the liquid-state conductive element.

* * * * *